United States Patent
Halleck et al.

(10) Patent No.: US 6,415,033 B1
(45) Date of Patent: Jul. 2, 2002

(54) PHYSIOLOGICAL CONDITION MONITORS UTILIZING VERY LOW FREQUENCY ACOUSTIC SIGNALS

(75) Inventors: Michael E. Halleck, Longmont; Michael D. Halleck, Northglenn, both of CO (US); Michael L. Lehrman, Washington, DC (US); Alan R. Owens, Longmont, CO (US)

(73) Assignee: iLife Systems, Inc., Dallas, TX (US)

( * ) Notice: Subject to any disclaimer, the term of this patent is extended or adjusted under 35 U.S.C. 154(b) by 0 days.

(21) Appl. No.: 09/536,093

(22) Filed: Mar. 24, 2000

Related U.S. Application Data

(63) Continuation-in-part of application No. 09/396,991, filed on Sep. 15, 1999.

(51) Int. Cl.$^7$ .............................. A61B 7/04; A61B 5/02
(52) U.S. Cl. .......................... 381/67; 381/56; 600/528; 600/586
(58) Field of Search .................... 381/67, 56, 58, 381/92, 94.2, 94.3, 98, 122, 355, 358; 600/528, 586; 181/131, 137; 340/669

(56) References Cited

U.S. PATENT DOCUMENTS

| | | | |
|---|---|---|---|
| 3,858,575 A | 1/1975 | Rose | 128/2.05 S |
| 4,306,567 A | 12/1981 | Krasner | 128/671 |
| 4,494,553 A | 1/1985 | Sciarra et al. | 128/721 |
| 4,672,976 A | 6/1987 | Kroll | 128/715 |
| 4,905,706 A | 3/1990 | Duff et al. | 128/701 |
| 4,934,375 A | 6/1990 | Cole et al. | 128/673 |
| 5,086,776 A | 2/1992 | Fowler, Jr. et al. | 128/661.09 |
| 5,450,854 A | 9/1995 | Kodama et al. | 128/732 |
| 5,550,902 A | 8/1996 | Abbruscato | 379/106 |
| 5,564,434 A | 10/1996 | Halperin et al. | 128/748 |
| 5,605,156 A | 2/1997 | Drzewiecki et al. | 128/672 |
| 5,825,895 A | 10/1998 | Grasfield et al. | 381/67 |
| 6,048,319 A | 4/2000 | Hudgins et al. | 600/528 |
| 6,099,486 A | 8/2000 | Fruscello | 600/586 |
| 6,213,955 B1 | 4/2001 | Karakasoglu et al. | 600/529 |
| 6,261,237 B1 | 7/2001 | Swanson et al. | 600/527 |

*Primary Examiner*—Xu Mei

(57) ABSTRACT

Physiological condition monitors utilizing very low frequency acoustic signals and signals indicative of body orientation are disclosed. The physiological condition monitors comprise a sensor that is capable of detecting low frequency acoustic signals in the frequency range of one tenth Hertz to thirty Hertz. The sensor comprises a chamber having portions that form a cavity and a low frequency microphone placed within the cavity. An alternate embodiment of the invention comprises a chamber having portions that form a resonant cavity, a microphone mounted in the resonant cavity, and a membrane that covers the resonant cavity. Low frequency acoustic signals that are incident on the membrane cause the membrane to move and amplify the acoustic signals within the resonant cavity. The sensor provides information concerning physiological conditions, such as respiration and cardiac activity. The sensor in a physiological condition monitor does not need to be directly coupled to the skin of the person being monitored. The physiological condition monitor simultaneously provides information concerning cardiac activity, and respiration activity, and the movement and position orientation of the monitored person's body.

36 Claims, 17 Drawing Sheets

PHYSIOLOGICAL CONDITION MONITORS UTILIZING VERY LOW FREQUENCY ACOUSTIC SIGNALS

RELATED APPLICATIONS

This patent application is a continuation in part of co-pending U.S. patent application Ser. No. 09/396,991 filed Sep. 15, 1999 by Lehrman et al. entitled "Systems for Evaluating Movement of a Body and Methods of Operating the Same." A related patent application by M. E. Halleck and M. D. Halleck has been filed concurrently with this patent application entitled "Sensor and Method for Detecting Very Low Frequency Acoustic Signals". Another related patent application by M. E. Halleck and M. D. Halleck has been filed concurrently with this patent application entitled "Apparatus and Method for Detecting Very Low Frequency Acoustic Signals". Another related patent application by M. E. Halleck and M. D. Halleck has been filed concurrently with this patent application entitled "System and Method for Remotely Monitoring At Least One Physiological Characteristic of a Child". Another related patent application by M. E. Halleck, M. D. Halleck and G. V. Halleck has been filed concurrently with this patent application entitled "System and Method for Seizing a Communication Channel in a Commercially Available Child Monitor".

TECHNICAL FIELD OF THE INVENTION

The present invention is directed, in general, to systems for monitoring physiological conditions of a person, and more specifically, to systems that are capable of monitoring respiration and cardiac activity, movement and position orientation of a body, and other types of physiological information utilizing very low frequency acoustic signals. The present invention is directed to an apparatus and method for detecting very low frequency acoustic signals that represent physiological activity. The present invention comprises a sensor and a method for detecting very low frequency acoustic signals in the frequency range of one tenth Hertz (0.1 Hz) to thirty Hertz (30.0 Hz). The sensor of the present invention is capable of obtaining physiological condition signals from a person without being directly coupled to the skin of the person.

BACKGROUND OF THE INVENTION

Microphones in physiological condition monitors are used to detect sounds that are indicative of physiological processes. Physiological condition monitors are capable of obtaining and recording signals indicative of a person's physiological processes. The most commonly monitored physiological processes are respiration and cardiac activity. Physiological condition monitors that monitor respiration and cardiac activity usually comprise one or more sensors coupled to the body of the person whose physiological conditions are to be measured. The sensors are capable of sensing changes in physical parameters that are caused by the person's respiration and cardiac activity. Physiological condition monitors measure and record waveform signals received from the sensors. Electrocardiogram (ECG) waveform signals are the most commonly used waveforms for measuring a person's cardiac activity. Respiration waveform signals may be electronically derived using techniques such as impedance pneumography or inductive plethysmography. Respiration waveform signals are used to measure a person's breathing rate and other types of information concerning respiration.

The present invention comprises a chamber and a microphone that is capable of detecting very low frequency acoustic signals. The present invention is capable of monitoring physiological conditions utilizing very low frequency acoustic signals. For purposes of illustration, the present invention will be described with reference to physiological condition monitors that are capable of monitoring respiration and cardiac activity. It is understood, however, that the present invention is not limited to use in respiration monitors, and is not limited to use in cardiac activity monitors, and is not limited to use in physiological condition monitors in general. The present invention may be used to detect, measure and record any type of very low frequency acoustic signal.

Low heart rate is referred to as bradycardia. High heart rate is referred to as tachycardia. Cessation of respiration is referred to as apnea. When a person exhibits apnea, bradycardia or tachycardia a life threatening condition very likely exists. Physiological condition monitors that are capable of continuously monitoring a person's respiration and cardiac activity are extremely useful for quickly detecting apnea, bradycardia or tachycardia. Such physiological condition monitors are also useful for quickly detecting other abnormal conditions such as a very slow breathing rate or a very high breathing rate.

Infants who are susceptible to sudden infant death syndrome are known to exhibit apnea and bradycardia. Physiological condition monitors that are capable of continually monitoring respiration and cardiac activity are particularly useful in the early detection of apnea or bradycardia in infants. Most physiological condition monitors are equipped with an alarm system to sound an alert when such conditions are detected.

A physiological condition monitor may be coupled directly to a person who is a patient in a hospital bed. In such an arrangement the waveform signals from the sensors coupled to the patient's body may be sent through wires directly to a detector circuit (and other circuitry) located in a console by the patient's bed. The wires attached to the patient restrict the patient's movements and frequently become tangled as the patient moves. The tangling of the wires can also result in the sensors becoming detached from the patient. The loss of sensor contact can set off an alarm signal.

In other cases it is more practical to provide one or more sensors located in a belt, harness or item of clothing that is to be worn by the person to be monitored. In this type of physiological condition monitor the waveform signal information from the sensors is transmitted via a radio frequency transmitter to a radio frequency receiver in a base station unit that is located away from the site of the physiological condition sensors. The base station unit contains circuitry for analyzing and recording the waveform signal information. The base station unit contains circuitry for detecting abnormal conditions in the person's breathing (such as apnea) or abnormal conditions in the person's cardiac activity (such as bradycardia or tachycardia). Because of the freedom of movement that this type of monitor provides, it is the preferred type of monitor for monitoring the physiological conditions of infants.

If the data that is acquired by the physiological condition monitor is not transmitted to the base station unit and recorded there, then the data may be recorded in a memory data storage device located within the physiological condition monitor. To preserve the freedom of movement that is provided by a monitor that is worn on a belt, harness or item of clothing, the memory data storage device within the physiological condition monitor must be battery powered.

Electrocardiogram (ECG) waveform signals are commonly used to obtain information concerning a person's cardiac activity. To obtain ECG waveforms an ECG sensor unit is coupled to the person whose cardiac activity is to be measured. The ECG sensor unit is coupled to the person via electrodes capable of receiving signals that are representative of cardiac activity directly from the person's body. In such an arrangement the electrodes must be attached directly to the person's skin in order to receive the signals. The ECG sensor unit receives the ECG electrical signals from the electrodes. The ECG signals received by the ECG sensor unit are then either recorded within the physiological condition monitor or transmitted to a base station unit.

It is also desirable to obtain information concerning the movement and position orientation of the monitored person's body. The correlation of information concerning a person's movement and position orientation with information concerning the person's cardiac activity and respiration activity can provide a very detailed picture of the person's physical condition.

It is possible to obtain information about cardiac activity from acoustic signals. For example, U.S. Pat. No. 4,306,567 to Krasner discloses a sensor apparatus coupled directly to the skin of a person. The Krasner sensor apparatus is capable of detecting acoustic signals from cardiac contractions within a frequency bandwidth between about thirty Hertz (30.0 Hz) and ninety Hertz (90.0 Hz). The acoustical energy associated with the cardiac contractions detected by the Krasner sensor apparatus exhibits a maximum signal-to-noise ratio at about forty five Hertz (45.0 Hz).

The Krasner sensor apparatus is also capable of detecting acoustic signals from breathing activity within a frequency bandwidth between about three hundred Hertz (300.0 Hz) and six hundred Hertz (600.0 Hz). The acoustical energy associated with the breathing activity detected by the Krasner sensor exhibits a maximum signal-to-noise ratio at about four hundred Hertz (400.0 Hz). The Krasner sensor simultaneously detects both the cardiac activity signals at about forty five Hertz (45.0 Hz) and the breathing activity signals at about four hundred Hertz (400.0 Hz) with a single sensor unit coupled directly to the skin.

Acoustic signals normally contain noise artifacts. We have determined that most of the noise artifacts present in acoustic signals due to respiration and cardiac activity may be eliminated by considering only the very low frequency components of acoustic signals. In particular, almost all noise artifacts that are present in acoustic signals that are due to respiration and cardiac activity may be totally eliminated by filtering out all components of the signal that are outside the frequency range of one tenth Hertz (0.1 Hz) to thirty Hertz (30.0 Hz). This is due to the fact most noise artifacts occur at frequencies that are higher than these frequencies.

We have also determined that sensor devices that are capable of detecting acoustic signals in the very low acoustic frequency range of one tenth Hertz (0.1 Hz) to thirty Hertz (30.0 Hz) do not need to be coupled directly to the skin of the person whose physiological conditions are being monitored. A sensor device that detects acoustic signals in the very low acoustic frequency range of one tenth Hertz (0.1 Hz) to thirty Hertz (30.0 Hz) in accordance with the principles of the present invention is capable of detecting indirect acoustic signals from the body of the monitored person through the monitored person's clothes.

For these reasons it is advantageous to be able to detect very low frequency acoustic signals in the range of one tenth Hertz (0.1 Hz) to thirty Hertz (30.0 Hz). It is also advantageous to have an apparatus for monitoring physiological conditions in which it is not necessary to couple a sensor unit directly to the skin of the person to be monitored. It is also advantageous to have an apparatus for monitoring physiological conditions that is capable of detecting acoustic signals through the monitored person's clothes.

SUMMARY OF THE INVENTION

The present invention comprises an improved apparatus and method for detecting very low frequency acoustic signals in the range of one tenth Hertz (0.1 Hz) to thirty Hertz (30.0 Hz). The very low frequency acoustic signals are useful in monitoring physiological conditions such as respiration and cardiac activity.

The present invention is capable of detecting signals in a frequency range that is lower than the range of frequencies previously used to detect acoustic signals for monitoring physiological conditions.

An advantageous embodiment of the present invention comprises a chamber and a microphone that is capable of detecting very low frequency acoustic signals in the range of one tenth Hertz (0.1 Hz) to thirty Hertz (30.0 Hz). An advantageous embodiment of the chamber of the present invention comprises a closed chamber containing a fluid. The fluid may be either a liquid or a gas. In most instances the fluid that is used is air. The walls of the chamber are not completely rigid. The walls of the chamber are capable of expanding and contracting (i.e., moving inwardly and outwardly with respect to the interior cavity of the chamber) in response to external inputs of mechanical energy that form waves of very low frequency acoustical energy within the chamber.

The mechanical energy from outside the chamber forms waves of very low frequency acoustical energy within the chamber and causes the walls of the chamber to expand and contract by extremely small amounts. The extremely small expansions and contractions of the walls of the chamber cause the molecules of fluid in the chamber (usually molecules of air) to move in low frequency acoustic waves throughout the cavity of the chamber.

The present invention further comprises a microphone within the chamber. The microphone is capable of detecting the low frequency acoustic waves of the molecules of fluid in the chamber that are caused by the mechanical energy that causes the walls of the chamber to expand and contract.

Prior art acoustic sensors directly detect higher frequency sounds that are made by the lungs during respiration or by the heart during cardiac activity. The sensor of the present invention, however, obtains information by detecting very low frequency signals caused by the motion of the chest during respiration and by detecting very low frequency signals associated with cardiac activity. Almost all of the noise components in an acoustic signal have frequencies that are above the very low frequency range. By using the method of the present invention to exclude the higher frequencies of sound (and noise), the sensor of the present invention eliminates almost all the noise artifacts from the acoustic signal.

The present invention is capable of detecting acoustic signals from cardiac activity within a frequency bandwidth between about ten Hertz (10.0 Hz) and thirty Hertz (30.0 Hz). The acoustical energy associated with the cardiac activity detected by the present invention exhibits a maximum signal-to-noise ratio at about sixteen Hertz (16.0 Hz)

The present invention is capable of detecting acoustic signals from respiration within a frequency bandwidth between about one tenth Hertz (0.1 Hz) and two Hertz (2.0 Hz). The acoustical energy associated with the respiration detected by the present invention exhibits a maximum signal-to-noise ratio at about one and one half Hertz (1.5 Hz).

It is a primary object of the present invention to provide an improved apparatus and method for detecting very low frequency acoustic signals in the frequency range of one tenth Hertz (0.1 Hz) to thirty Hertz (30.0 Hz).

It is also an object of the present invention to provide an improved physiological condition monitor capable of detecting very low frequency acoustic signals in the frequency range of one tenth Hertz (0.1 Hz) to thirty Hertz (30.0 Hz) that are indicative of physiological conditions.

It is also an object of the present invention to provide an improved physiological condition monitor with a sensor unit capable of detecting very low frequency acoustic signals indicative of physiological conditions where the sensor unit is not coupled directly to the skin of the person being monitored.

It is also an object of the present invention to provide an improved physiological condition monitor with a sensor unit capable of detecting very low frequency acoustic signals indicative of physiological conditions where the sensor unit is capable of detecting such signals through the clothes of the person being monitored.

It is also an object of the present invention to provide an improved physiological condition monitor capable of detecting acoustic signals from cardiac activity within a frequency bandwidth between about ten Hertz (10.0 Hz) and thirty Hertz (30.0 Hz).

It is a further object of the present invention to provide an improved physiological condition monitor capable of detecting acoustic signals from respiration within a frequency bandwidth between about one tenth Hertz (0.1 Hz) and two Hertz (2.0 Hz).

It is also an object of the present invention to provide an improved physiological condition monitor that is capable of simultaneously obtaining (1) information concerning a person's cardiac activity, and (2) information concerning a person's respiration activity, and (3) information concerning the movement and position orientation of the monitored person's body.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description, it may be advantageous to set forth definitions of certain words and phrases used throughout this patent document: the terms "include" and "comprise" and derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware, or software, or some combination of at least two of the same. It should be noted that the functionality associated with any particular controller may be centralized or distributed, whether locally or remotely. Definitions for certain words and phrases are provided throughout this patent document. Those of ordinary skill in the art should understand that in many, if not most, instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION

FIGS. 1 through 24, discussed below, and the various embodiments used to describe the principles of the present invention in this patent document are by way of illustration only and should not be construed in any way to limit the scope of the invention. Those skilled in the art will understand that the principles of the present invention may be implemented in a suitably modified sensor or in a suitably modified physiological condition monitor.

Figure 1:
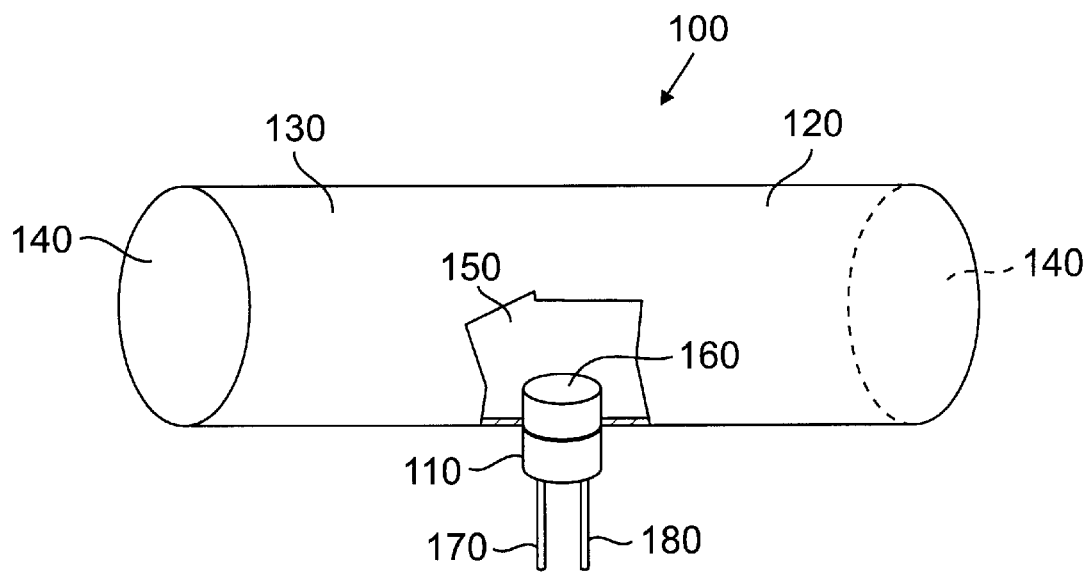
FIG. 1 is a partially cutaway view showing one embodiment of the sensor of the present invention and showing the sensor chamber as a tube and showing the placement of the microphone of the present invention in one of the side walls of the sensor chamber.
Figure 2:
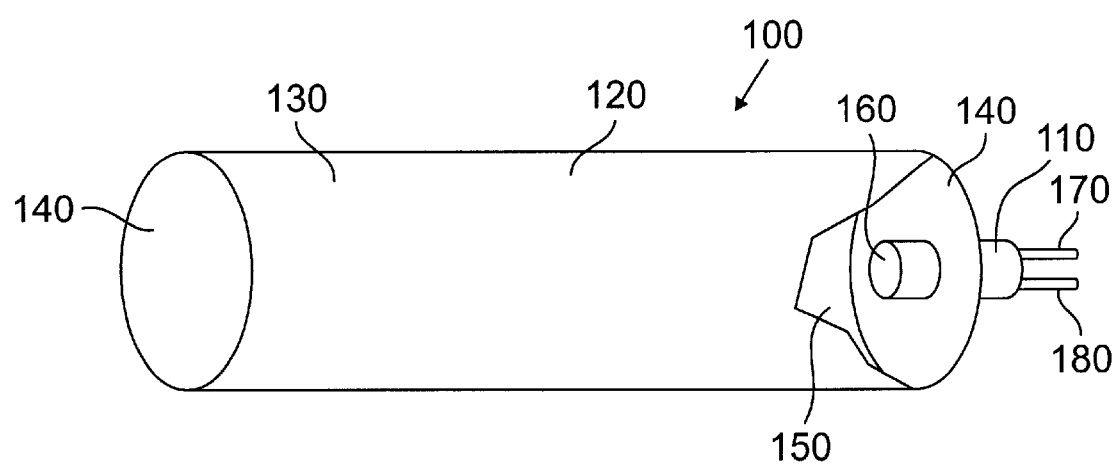
FIG. 2 is a partially cutaway view showing another embodiment of the sensor of the present invention and showing the sensor chamber as a tube and showing the placement of the microphone of the present invention in one of the end walls of the sensor chamber.

FIG. 1 is a partially cutaway view showing an advantageous embodiment of sensor 100 of the present invention. Sensor 100 comprises a chamber 120 and a microphone 110. In this embodiment chamber 120 comprises a hollow tube having side walls 130 and end walls 140 that form cavity 150 within chamber 120. Cavity 150 of chamber 120 is filled with a fluid (not shown). The connections between side walls 130 and end walls 140 are sealed to prevent the escape of the fluid from cavity 150. The fluid may be either a liquid or a gas. In most instances the fluid that is used is air.

When the fluid that is used is air, the connections between side walls 130 and end walls 140 are not hermetically sealed. A small amount of air may pass through the connections between side walls 130 and end walls 140 to adjust for variations in ambient air pressure in the atmosphere.

Microphone 110 is mounted within chamber 120 so that the face 160 of microphone 110 is within the fluid in cavity 150 of chamber 120. Microphone 110 may be mounted at any position within chamber 120. In one advantageous embodiment of the present invention shown in FIG. 1 microphone 110 is mounted within one of the side walls 130 of chamber 120. In an alternate advantageous embodiment of the present invention shown in FIG. 2 microphone 110 is mounted within one of the end walls 140 of chamber 120. Microphone 110 also has microphone output cables, 170 and 180, for coupling microphone 110 to other electronic equipment (not shown in FIG. 1 or FIG. 2).

The side walls 130 (and end walls 140) of chamber 120 are constructed of material that is not completely rigid. The material used to construct the walls, 130 and 140, may be thin metal or plastic. Because the walls, 130 and 140, are not completely rigid, they are capable of expanding and contracting (i.e., moving inwardly and outwardly) with respect to the interior of cavity 150 of chamber 120. The ability of the walls, 130 and 140, of sensor 100 to expand and contract in response to the presence of waves of low frequency acoustical energy in chamber 120 is a key feature of the present invention.

When acoustical energy from a source (not shown) reaches chamber 120 of sensor 100 the acoustical energy contains both high frequency acoustic signal components and low frequency acoustic signal components. The walls 130 and the end walls 140 of chamber 120 of sensor 100 expand and contract in response to the presence of the very low frequency acoustic signal components. The presence of waves of very low frequency acoustic energy in chamber 120 of sensor 100 cause the walls, 130 and 140, of chamber 120 to expand and contract by extremely small amounts.

The extremely small expansions and contractions of the walls, 130 and 140, of chamber 120 of sensor 100 in response to the presence of very low frequency acoustic signals cause the molecules of fluid in chamber 120 (usually molecules of air) to move in low frequency waves throughout the cavity 150 of chamber 120. Microphone 110 is capable of detecting the low frequency waves of molecules of fluid in chamber 120 that are caused by the low frequency acoustic signal components in the acoustical energy that cause the walls, 130 and 140, of chamber 120 to expand and contract.

When microphone 110 receives low frequency acoustic signals then microphone 110 generates electronic signals indicative of the intensity of the low frequency acoustic signals. Electronic processing circuits (shown in FIGS. 6A, 6B and 6C) in a physiological condition monitor 700 (shown in FIG. 7) are coupled to microphone 110 through microphone output cables, 170 and 180, to receive and analyze the electronic signals that are indicative of the intensity of the low frequency acoustic signals.

The electronic processing circuits comprise electronic filters for filtering out all components of the signal that are outside the frequency range of one tenth Hertz (0.1 Hz) to thirty Hertz (30.0 Hz). The electronic processing circuits also comprise electronic filters for filtering out all components of the signal that are outside the frequency range of one tenth Hertz (0.1 Hz) to two Hertz (2.0 Hz) to obtain a signal indicative of respiration. The electronic processing circuits also comprise electronic filters for filtering out all components of the signal that are outside the frequency range of ten Hertz (10.0 Hz) to thirty Hertz (30.0 Hz) to obtain a signal indicative of cardiac activity.

Prior art sensors directly detect higher frequency sounds that are made by the lungs during respiration or by the heart during cardiac activity. Sensor 100 of the present invention, however, obtains information by detecting very low frequency signals caused by the motion of the chest during respiration and by detecting very low frequency signals associated with cardiac activity. Almost all of the noise components in an acoustic signal have frequencies that are above the very low frequency range. Using the method of the present invention to exclude the higher frequencies of sound (and noise), sensor 100 of the present invention eliminates almost all the noise artifacts from the acoustic signal.

Figure 3:
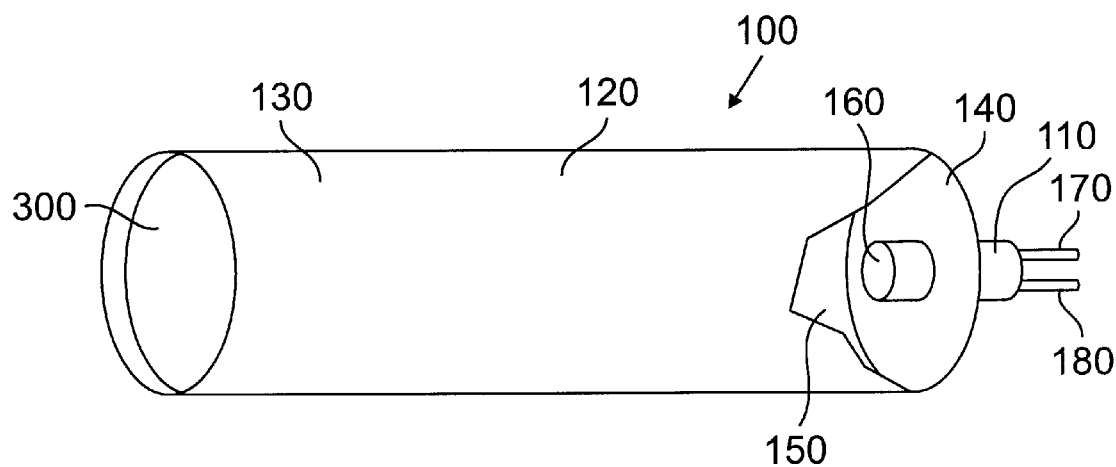
FIG. 3 is a partially cutaway view showing another embodiment of the sensor of the present invention and showing the sensor chamber as a tube with one open end and showing the placement of the microphone of the present invention in the closed end of the sensor chamber.

An alternate advantageous embodiment of the present invention is shown in FIG. 3. The embodiment shown in FIG. 3 is similar to that shown in FIG. 2 except that chamber 120 of sensor 100 comprises an open ended tube having portions that form an aperture 300. In this embodiment cavity 150 of chamber 120 has access to the surrounding atmosphere through aperture 300 in the open end of the tube. In the embodiment shown in FIG. 3 microphone 110 is placed within the end wall 140 of the closed end of the tube.

Alternatively, microphone 110 could be placed within a side wall 130 of an open ended tube. This embodiment shows that it is possible to practice the invention where the fluid in chamber 120 is air that has access to the air of the surrounding environment.

Although chamber 120 of sensor 100 has been shown in the shape and form of a tube, it is clear that the invention may be practiced with a chamber 120 of sensor 100 that has a different type of shape and form. One such alternate embodiment of the present invention is shown in FIG. 4.

Figure 4:
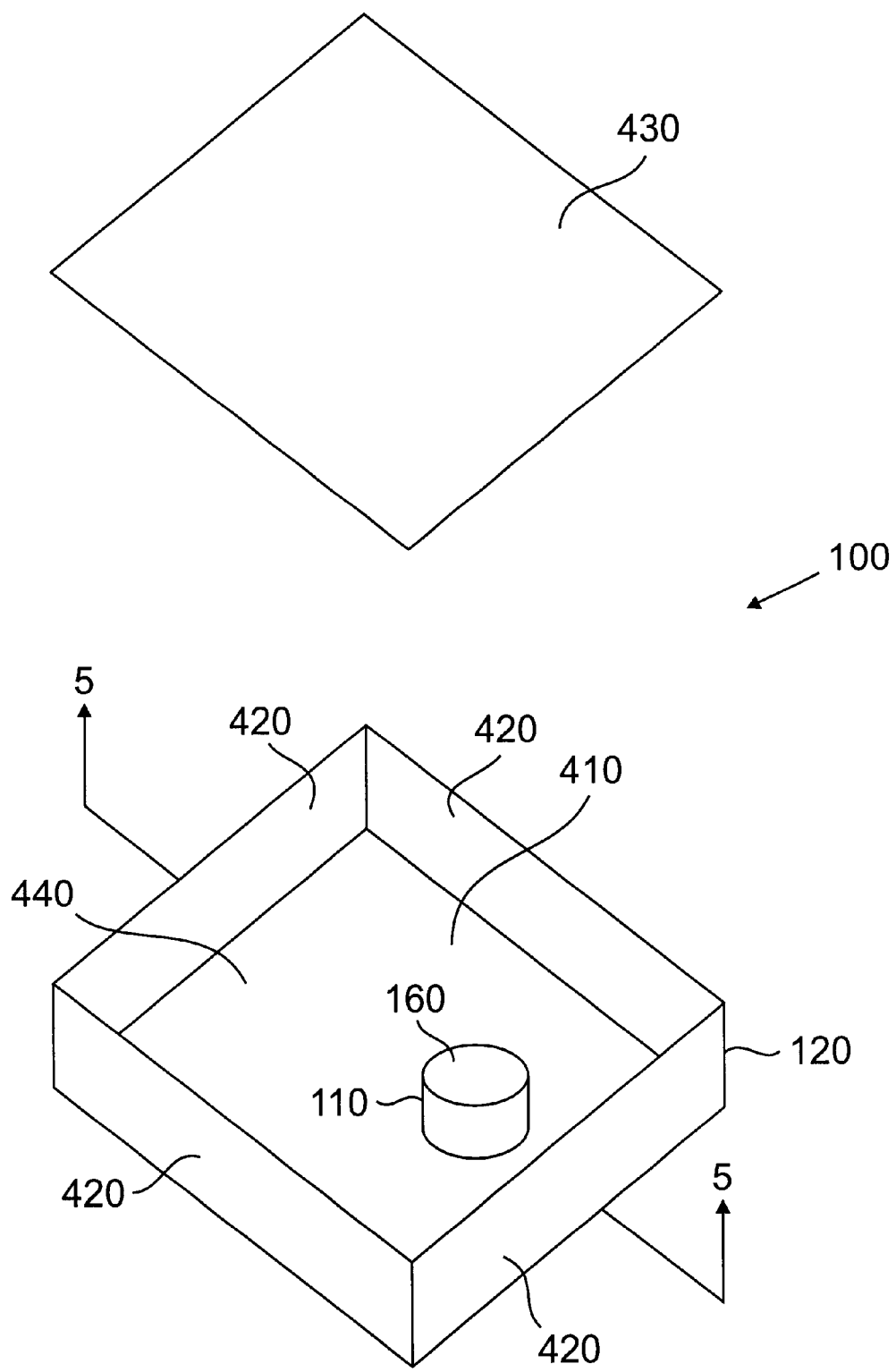
FIG. 4 is an exploded view showing another embodiment of the sensor of the present invention and showing the sensor chamber as a rectangular box and showing the placement of the microphone of the present invention within the rectangular box.

FIG. 4 shows an exploded view of an alternate advantageous embodiment of sensor 100 of the present invention. Sensor 100 comprises microphone 110 mounted within chamber 120. Microphone 110 may be mounted at any position on the interior surface of the bottom 410 of chamber 120. In the embodiment of the invention shown in FIG. 4 the shape of chamber 120 is rectangular. However, the shape of chamber 120 may be circular, elliptical, or of irregular shape. The height of the walls 420 of chamber 120 are greater than the height of microphone 110 so that the face 160 or microphone 110 is contained within chamber 120.

Membrane 430 covers the top of chamber 120. Membrane 430 has a shape that matches the shape of the top of chamber 120. In the embodiment of sensor 100 shown in FIG. 4, that shape is rectangular. When membrane 430 is attached to the top edges of the walls 420 of chamber 120, then a cavity 440 is formed between membrane 430 and walls 420 and bottom 410 of chamber 120. In one advantageous embodiment of the present invention, the height of the walls 420 are only slightly greater than the height of microphone 110 so that the face 160 of microphone 110 is positioned near membrane 430.

In one advantageous embodiment of the present invention membrane 430 is made of urethane. However, membrane 430 may also be made of other suitable materials. Before membrane 430 is attached to the top of chamber 120 membrane 430 is slightly stretched. The slight stretching of membrane 430 is to make membrane 430 taut across the top of chamber 120.

When sensor 100 is used to detect acoustic signals indicative of physiological conditions, chamber 120 is placed next to the body (not shown) of the person whose physiological conditions are being monitored. Chamber 120 is placed with the outer surface of membrane 430 adjacent to a selected area of the body. It is not necessary that membrane 430 touch the skin of the body. There may be a layer of clothing between the skin of the body and membrane 430. Membrane 430 is thereby acoustically coupled to the area of the body where membrane 430 is placed.

Membrane 430 acquires very low frequency acoustic signals in the form of vibrations from the area of the body to which it is acoustically coupled. That is, as the very low frequency acoustic vibrations from the body impinge upon membrane 430 they cause membrane 430 to vibrate. These vibrations of membrane 430 cause the very low frequency acoustic vibrations to pass into cavity 440 of chamber 120. The very low frequency acoustic vibrations resonate within the enclosed space of cavity 440.

Figure 5:
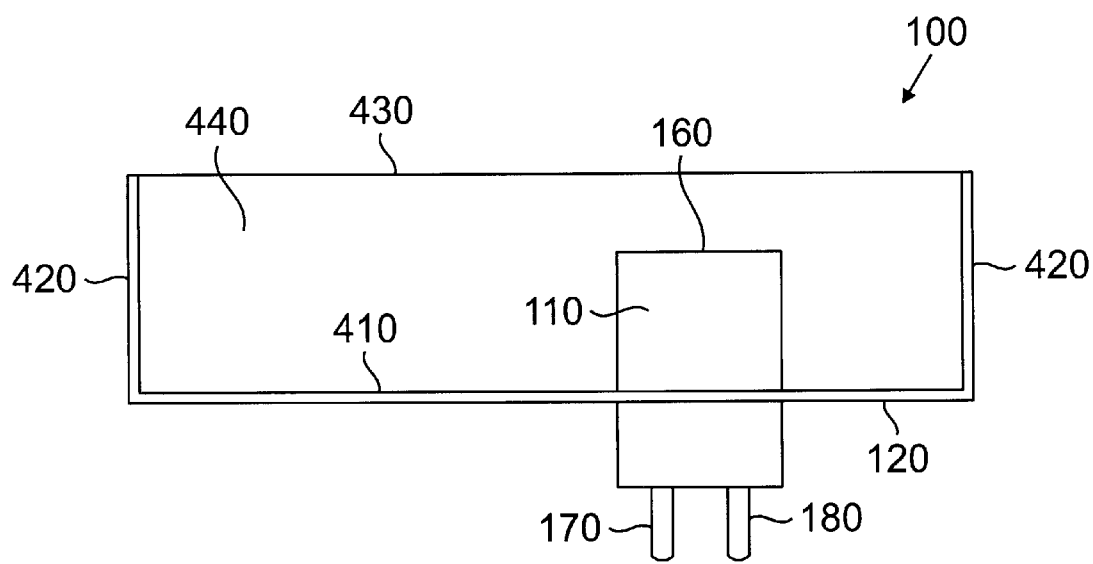
FIG. 5 is a cross sectional view of the embodiment of the sensor of the present invention shown in FIG. 4 taken along line 5—5 of FIG. 4.

FIG. 5 shows a cross sectional view of sensor 100 showing cavity 440 and one possible location for the placement of microphone 110 within cavity 440. Microphone 110 detects the very low frequency acoustic vibrations that are resonating within cavity 440.

The interaction of membrane 430 and resonant cavity 440 increases the amplitude of the very low frequency acoustic signals from the body so that microphone 110 may more easily detect the signals. The interaction of membrane 430 and resonant cavity 440 accomplishes this increase in acoustic signal strength by forming an acoustic echo chamber in which membrane 430 acts as a drumhead and resonant cavity 440 acts as a drum. The resonance of the very low frequency acoustic signals within resonant cavity 440 causes the amplitudes of the acoustic waves within resonant cavity 440 to combine in phase and thereby increase the acoustic signal strength of the acoustic signals that were originally incident on membrane 430.

The increase in amplitude of the signals provided by the interaction of membrane 430 and resonant cavity 440 enables microphone 110 to efficiently detect signals in the very low frequency range of one tenth Hertz (0.1 Hz) to thirty Hertz (30.0 Hz). This very low frequency range includes the very low frequency range used to detect respiration signals (i.e., one tenth Hertz (0.1 Hz) to two Hertz (2.0 Hz)) and the very low frequency range used to detect cardiac information signals (i.e., ten Hertz (10.0 Hz) to thirty Hertz (30.0 Hz)). The interaction of membrane 430 and resonant cavity 440 assists microphone 110 in detecting very low acoustic signals in the required signal ranges.

To improve reception of the very low frequency acoustic signals, the surface area of membrane 430 is larger than the surface area of the face 160 of microphone 110. In an advantageous embodiment of the present invention the surface area of membrane 430 is at least five (5) times greater than the surface area of the face 160 of microphone 110. The presence of membrane 430 significantly increases the area which may be acoustically coupled to microphone 110. The relatively large area of membrane 430 permits larger areas of a body to be analyzed than would otherwise be possible.

When microphone 110 receives low frequency acoustic signals then microphone 110 generates electronic signals indicative of the intensity of the low frequency acoustic signals. As described more fully below, electronic processing circuits in physiological condition monitor 700 are coupled to microphone 110 through microphone output cables, 170 and 180, to receive and analyze the electronic signals that are indicative of the intensity of the low frequency acoustic signals.

Figure 6A:
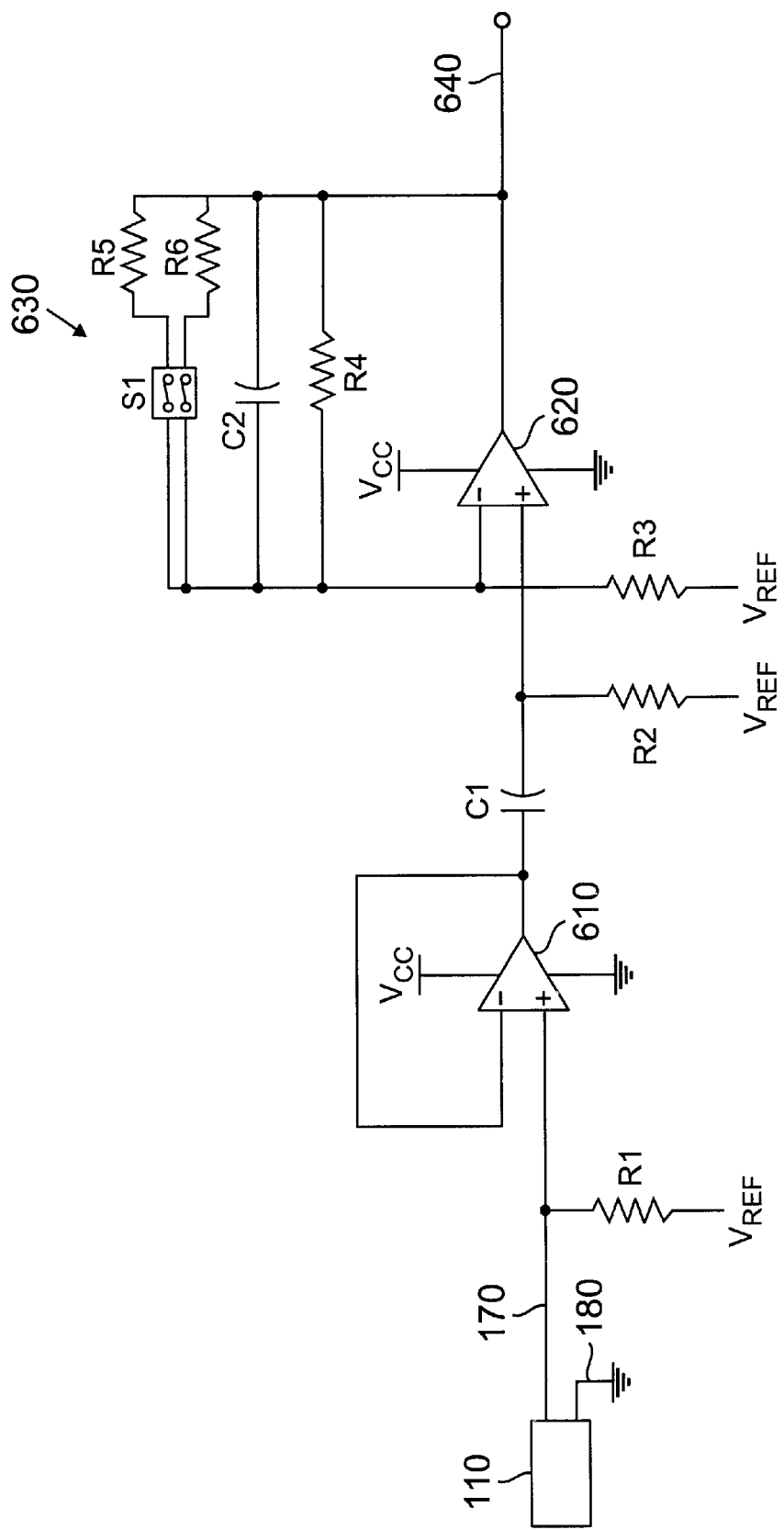
FIGS. 6A, 6B and 6C are circuit diagrams of an advantageous embodiment of circuitry for processing electrical signals from the microphone of the present invention.
Figure 6B:
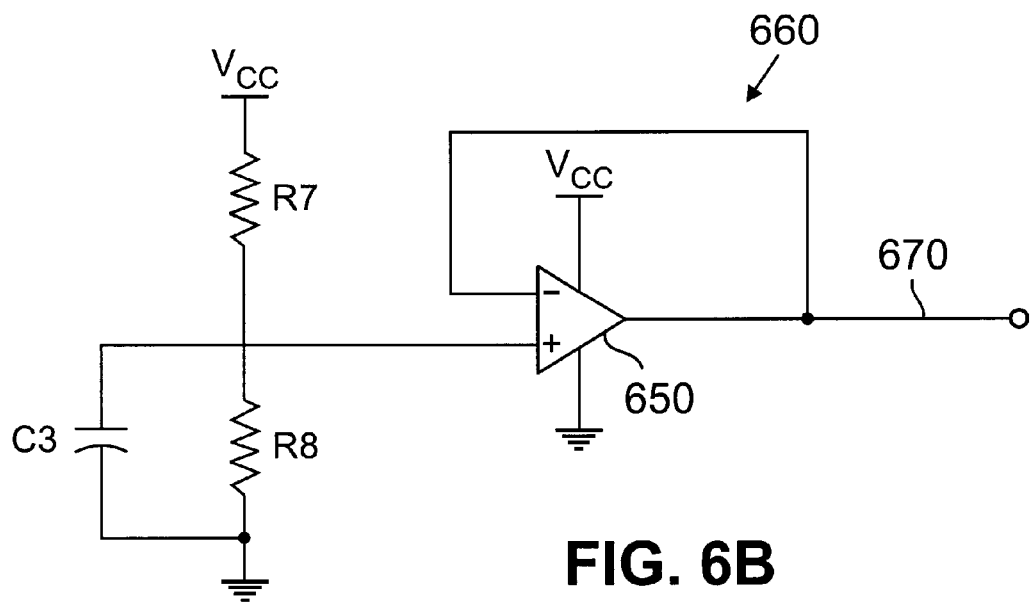
Figure 6C:
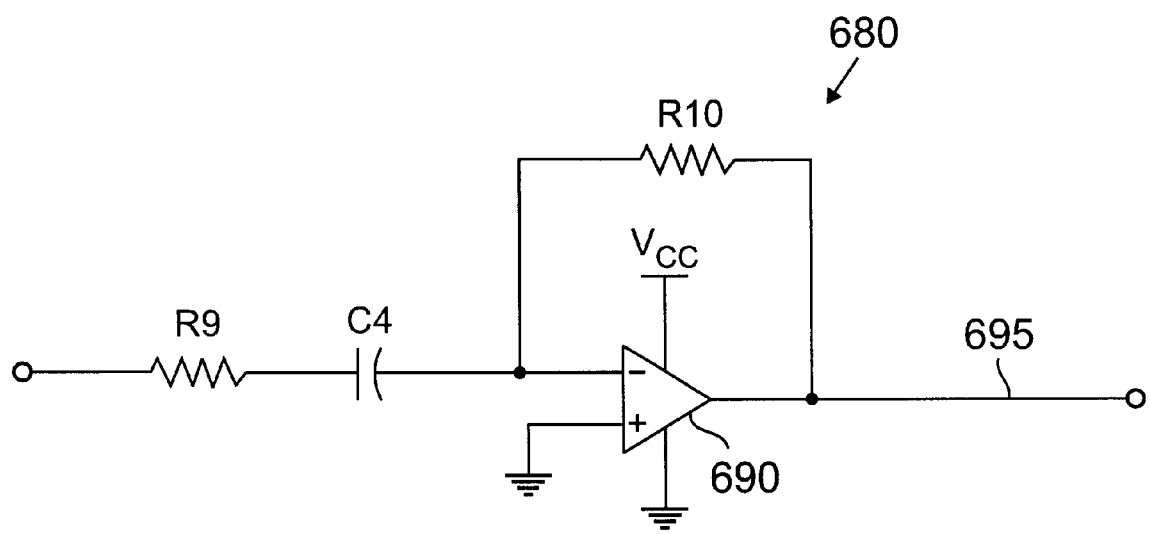

FIGS. 6A, 6B and 6C illustrate circuit diagrams of an advantageous embodiment of circuitry for processing electrical signals from the microphone of the present invention. As shown in FIG. 6A, microphone output cable 180 is grounded and microphone output cable 170 is coupled to the positive input of operational amplifier 610. The output of operational amplifier 610 is fed back to the negative input of operational amplifier 610 in order to configure operational amplifier 610 as a voltage follower (also known as a buffer amplifier circuit). The voltage follower configuration of operational amplifier 610 acts as a current amplifier for the signal current from microphone 110. The signal current that is output from operational amplifier 610 is an amplified version of the signal current from microphone 110. Operational amplifier 610 may be of the type manufactured by Texas Instruments Corporation with product model number TLV2211.

One end of a resistor R1 having a very large value is coupled to the signal line between microphone 110 and operational amplifier 610. The other end of resistor R1 is coupled to a reference voltage $V_{REF}$. A typical value of R1 is one teraohm (1.0 T). One teraohm is equal to one million million ohms. A very large resistance is needed to facilitate the signal processing of the very low frequency signals detected by microphone 110. A typical value for reference voltage $V_{REF}$ is one half of the voltage of the power supply battery.

The output signal from operational amplifier 610 is coupled via capacitor C1 to the positive input of operational amplifier 620. Operational amplifier 620 forms part of low bandpass filter circuit 630. Operational amplifier 620 may be of the type manufactured by Texas Instruments Corporation with product model number TLV2211.

A typical value of capacitor C1 is forty seven hundredths of a microfarad (0.47 μF). One end of resistor R2 is coupled to the signal line between capacitor C1 and operational amplifier 620.

The other end of resistor R2 is coupled to the reference voltage $V_{REF}$. A typical value of R2 is five and one tenth megohms (5.1 M).

Low bandpass filter circuit 630 comprises a double pole switch S1 for adjusting the value of the resistance that is coupled in parallel with capacitor C2. When both poles of switch S1 are in the open position, both resistor R5 and resistor R6 are excluded from the circuit. Resistor R5 or resistor R6 (or both) can be selectively included in the circuit by closing the appropriate pole (or both poles) of switch S1.

A typical value for capacitor C2 is thirty three thousands of a microfarad (0.033 μF). A typical value for resistor R3 is five hundred ten kilohms (510.0 K) and a typical value for resistor R4 is two megohms (2.0 M). A typical value for resistor R5 is one megohm (1.0 K) and a typical value for resistor R6 is two megohms (2.0 M).

The output of operational amplifier 620 of low bandpass filter circuit 630 appears at the output terminal 640.

FIG. 6B illustrates reference voltage generator circuit 660. The output of reference voltage generator circuit 660 is the reference voltage $V_{REF}$. The battery voltage $V_{cc}$ is coupled via resistor R7 to the positive input of operational amplifier 650. Operational amplifier 650 forms part of the reference voltage generator circuit 660. Operational amplifier 650 may be of the type manufactured by Texas Instruments Corporation with product model number TLV2211. A typical value of resistor R7 is five and one tenth megohms (5.1 M).

One end of resistor R8 is coupled to the signal line between resistor R7 and operational amplifier 650. The other end of resistor R8 is grounded. Capacitor C3 is coupled in parallel with resistor R8. A typical value of resistor R8 is five and one tenth megohms (5.1 M). A typical value for capacitor C3 is one hundredth of a microfarad (0.01 μF).

The output of operational amplifier 650 of reference voltage generator circuit 660 appears at the output terminal 670 as $V_{REF}$. The reference voltage $V_{REF}$ is coupled to the ends of resistor R1, resistor R2 and resistor R3 as indicated in FIG. 6A.

FIG. 6C shows high bandpass filter circuit 680. High bandpass filter circuit 680 comprises operational amplifier 690. Operational amplifier 690 may be of the type manufactured by Texas Instruments Corporation with product model number TLV2211.

One end of resistor R9 is coupled to the signal line between capacitor C1 and operational amplifier 620. The other end of resistor R9 is coupled to capacitor C4. A typical value of resistor R9 is thirty three kilohms (33 K). A typical value of capacitor C4 is forty seven hundredths of a microfarad (0.47 μF). The output of capacitor C4 is coupled to the negative input of operational amplifier 690. The output of operational amplifier 690 is fed back via resistor R10 to the negative input of operational amplifier 690. The positive input of operational amplifier 690 is grounded. the A typical value of resistor R10 is thirty three kilohms (33 K).

The output of operational amplifier 690 of high bandpass filter circuit 680 appears at the output terminal 695. The function of high bandpass filter circuit 680 may also be accomplished by utilizing digital signal processing methods. For example, the Fast Fourier Transform method may be utilized to perform the function of high bandpass filter 680.

Figure 7:
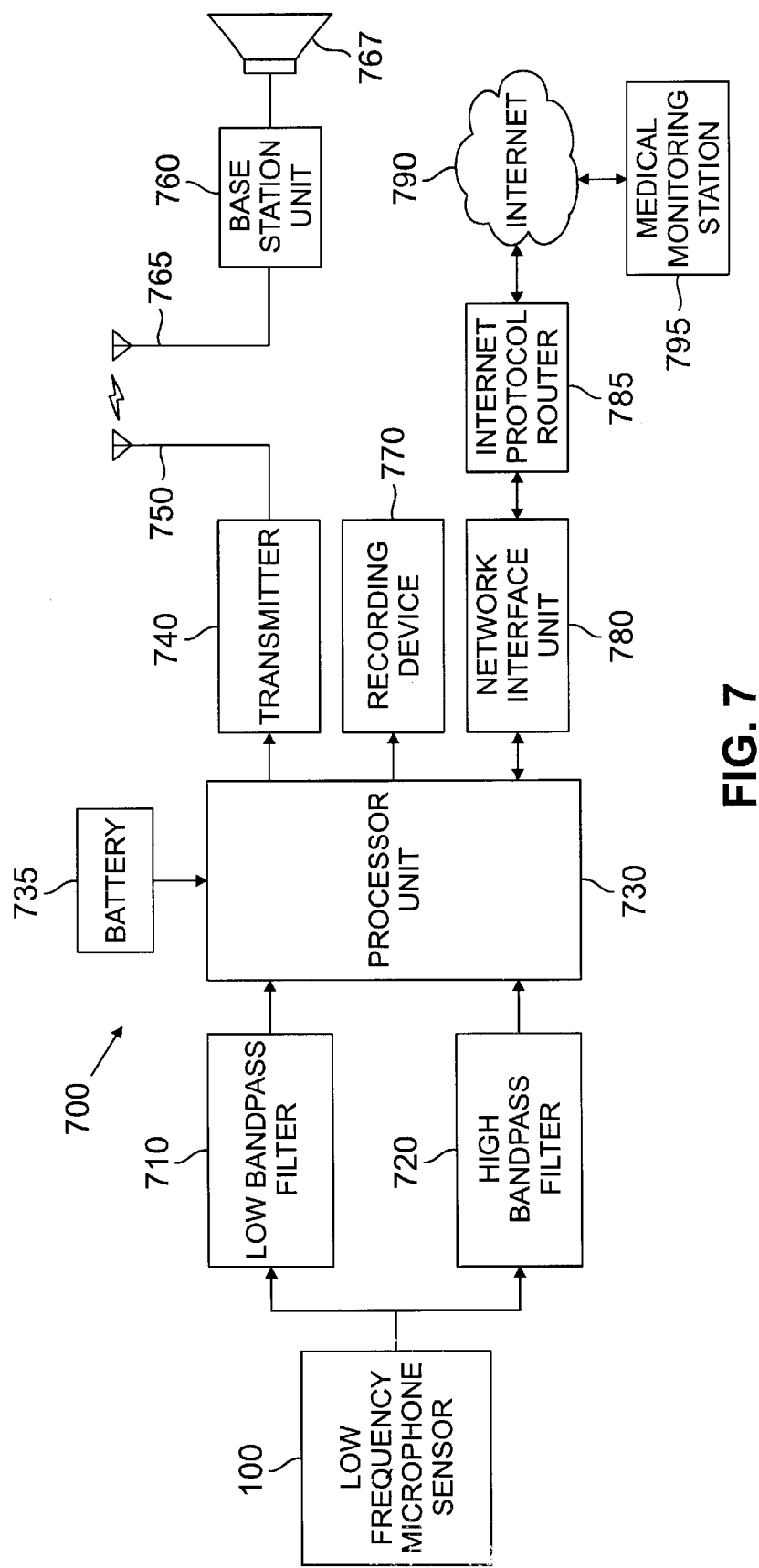
FIG. 7 is a block diagram of an advantageous embodiment of a physiological condition monitor of the present invention.

FIG. 7 is a block diagram of an advantageous embodiment of a physiological condition monitor 700 that utilizes the low frequency microphone sensor 100 of the present invention. As previously described, low frequency microphone sensor 100 receives low frequency signals from the body (not shown) of a person whose physiological conditions are being monitored. Low frequency microphone sensor 100 detects and amplifies those signals as previously described.

As shown in FIG. 7, the output of low frequency microphone sensor 100 is coupled to an input of low bandpass filter 710. Low bandpass filter 710 screens out all frequencies except those frequencies in the frequency bandwidth range from one tenth Hertz (0.1 Hz) to two Hertz (2.0 Hz). Low bandpass filter 710 may comprise conventional electronic filter circuits. Low bandpass filter 710 may also comprise electronic circuitry that utilizes computer software to achieve the bandpass filter function by digital signal processing. The output of low bandpass filter 710 is a digitally encoded very low frequency signal representative of the respiration of the person being monitored.

The output of low frequency microphone sensor 100 is also coupled to an input of high bandpass filter 720. High bandpass filter 720 screens out all frequencies except those frequencies in the frequency bandwidth range from ten Hertz (10.0 Hz) to thirty Hertz (30.0 Hz). High bandpass filter 720 may comprise conventional electronic filter circuits. High bandpass filter 720 may also comprise electronic circuitry that utilizes computer software to achieve the bandpass filter function by digital signal processing. The output of high bandpass filter 720 is a digitally encoded very low frequency signal representative of the cardiac activity of the person being monitored.

The output of low bandpass filter 710 and the output of high bandpass filter 720 are coupled to processor unit 730. Processor unit 730 is capable of receiving digitally encoded signals from low bandpass filter 710 and from high bandpass filter 720. Battery 735 is coupled to processor unit 730 and is capable of supplying electrical power for the operation of processor unit 730. Although battery 735 is shown coupled only to processor unit 730 in FIG. 7, battery 735 is connected to and provides power to all components of physiological condition monitor 700 through other electrical connections (not shown). Processor unit 730 is capable of detecting a signal from battery 735 that indicates that the voltage level of battery 735 is low.

In one embodiment of the present invention, processor unit 730 is coupled to radio frequency transmitter 740, which is itself coupled to antenna 750. Processor unit 730 is capable of selectively causing radio frequency transmitter 740 to transmit digitally encoded signals from low band pass filter 710 and digitally encoded signals from high band pass filter 720 to base station unit 760 via transmitter 740 and antenna 750. The digitally encoded signals are received by base station unit 760 via antenna 765. The received signals may then be displayed and analyzed at base station unit 760.

Processor unit 730 is capable of causing radio frequency transmitter 740 to transmit a signal to base station unit 760 that indicates that the voltage level of battery 735 is low. Processor unit 730 is also capable of causing radio frequency transmitter 740 to transmit a signal to base station unit 760 that indicates that processor unit 730 is not receiving signals from low bandpass filter 710 or from high bandpass filter 720. That is, processor unit 730 can transmit to base station unit 760 a signal indicating that one (or both) of the physiological conditions (breathing and heartbeat) is not being monitored.

Base station unit 760 is capable of sounding an alarm if an analysis of the received signals indicates an abnormal condition in the person being monitored. Base station unit 760 comprises speaker 767 which may be activated to sound an alarm when base station unit 760 receives one or more signals indicating that (1) the person's breathing is irregular or has stopped, (2) the person's heartbeat is irregular or has stopped, or (3) the person's breathing is not being monitored, or (4) the person's heartbeat is not being monitored, or (5) the battery voltage level is too low. Base station 760 is to be placed where a care giver who is monitoring base station 760 can hear the alarm whenever the alarm sounds.

In this manner, the person's care giver can immediately respond to the alarm to determine what condition exists. If the person is in physiological distress, the person's care giver can immediately attempt to relieve that distress. For example, if the person has ceased breathing, the care giver could immediately administer cardio-pulmonary resuscitation (CPR) to the person. If the alarm indicates a low battery or failure of monitoring function, remedial steps can be taken immediately.

In one advantageous embodiment of physiological condition monitor 700, a monitor housing 800 contains low frequency microphone sensor 100, low bandpass filter 710, high bandpass filter 720, processor unit 730, battery 735, transmitter 740 and antenna 750. An advantageous embodiment of monitor housing 800 will be described in connection with FIGS. 8 to 21. Monitor housing 800 is capable of being coupled to a belt, harness or item of clothing that may be worn by the person being monitored. In this embodiment of physiological condition monitor 700 the movements of the person being monitored are not restricted.

In an alternate advantageous embodiment of physiological condition monitor 700 processor unit 730 is coupled to recording device 770. Processor unit 730 sends digitally encoded signals from low band pass filter 710 and digitally encoded signals from high band pass filter 720 to recording device 770. Recording device 770 is preferably a non-volatile data storage device such as a magnetic tape recorder or a flash memory data storage card. A non-volatile data storage device is a device that retains the data stored in it when external power to the device is shut off.

In an additional advantageous embodiment of physiological condition monitor 700 processor unit 730 is coupled to network interface unit 780. Network interface unit 780 is capable of being coupled to a computer network such as a local area network (LAN), or a wide area network (WAN), or the Internet. The connection of network interface unit 780 to a computer network may be a wired connection or wireless connection. In FIG. 7 network interface unit 780 is shown coupled to the Internet 790 via an Internet protocol router 785. Processor unit 730 sends digitally encoded signals from low band pass filter 710 and digitally encoded signals from high band pass filter 720 to network interface unit 780. Network interface unit 780 adapts the data to be transmitted via Internet protocol router 785 to the Internet 790. In this manner the data can be sent to medical monitoring station 795 at a remote location. Medical monitoring station 795 can be located in a hospital, a doctor's office, a clinic, a care giver facility, or any similar type of location.

In an alternate advantageous embodiment of physiological condition monitor 700 processor unit 730 is not coupled to transmitter 740 and to antenna 750. Instead processor unit 730 is coupled directly by wire to a wired base station unit (not shown) of the type described above. The wired base station unit is usually located in a console by the bed or chair of the person being monitored. As in the previously described case of base station unit 760, the wired base station unit is capable of displaying and analyzing digitally encoded signals from processor unit 730. The wired base station unit is capable of sounding an alarm if an analysis of the digitally encoded signals indicates an abnormal condition in the person being monitored. In this embodiment the wires coupling the physiological condition monitor 700 to the wired base unit do restrict the movements of the person being monitored.

Figure 8:
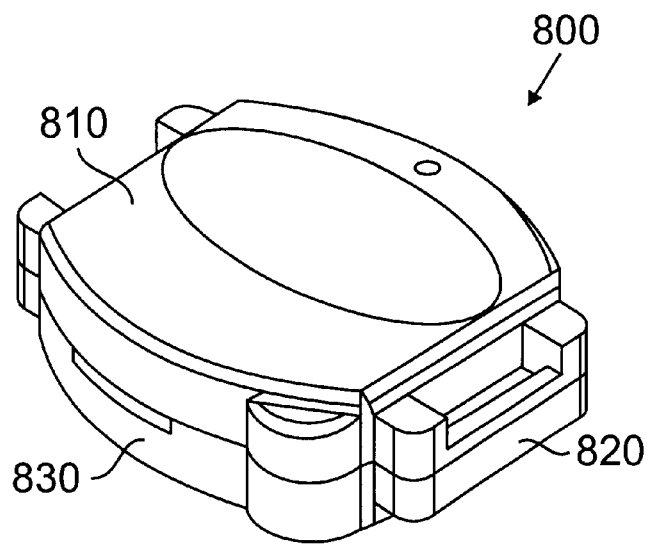
FIG. 8 is a perspective top view of an advantageous embodiment of the monitor housing of the physiological condition monitor of the present invention.
Figure 9:
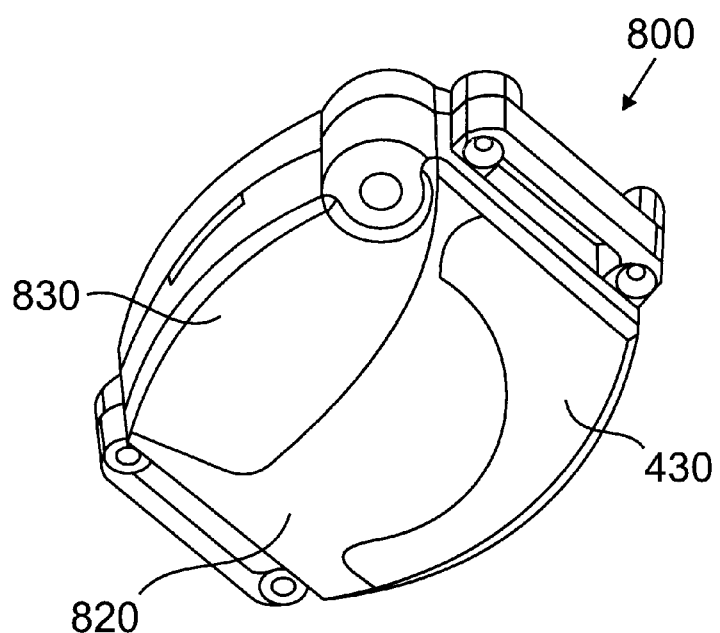
FIG. 9 is a perspective bottom view of the advantageous embodiment of the monitor housing of the physiological condition monitor of the present invention shown in FIG. 8.

FIGS. 8 though 21 depict an advantageous embodiment of monitor housing 800 of physiological condition monitor 700 that is shown in FIG. 7. FIG. 8 shows a perspective top view of monitor housing 800. FIG. 9 shows a perspective bottom view of monitor housing 800. The top half of monitor housing 800 comprises a top housing 810 and the bottom half of monitor housing 800 comprises a bottom housing 820. As shown in FIG. 8 and FIG. 9, top housing 810 and bottom housing 820 fit together to enclose the elements of physiological condition monitor 700. Top housing 810 and bottom housing 820 are formed having portions that define a cavity within monitor housing 800 to receive battery 735 that is shown in FIG. 7. In this embodiment battery 735 is a flat, cylindrically symmetrical, coin-shaped battery of the type commonly used in cameras and other portable electronic equipment.

Bottom housing 820 is formed having portions that receive a battery door 830 that may be opened and closed to allow access to place and remove battery 735 within the interior of monitor housing 800. Battery door 830 is pivotally connected to bottom housing 820 and may be opened and closed by pivotally moving battery door 830 with respect to bottom housing 820. Battery door 830 is shown in closed position in FIG. 9.

The outer surface of membrane 430 of low frequency microphone sensor 100 is also shown in FIG. 9. In this advantageous embodiment of the present invention, membrane 430 (and cavity 440) has an geometrically irregular shape. The shape generally comprises two curves of different radii spaced apart and bounded on the ends by relatively flat surfaces.

Figure 10:
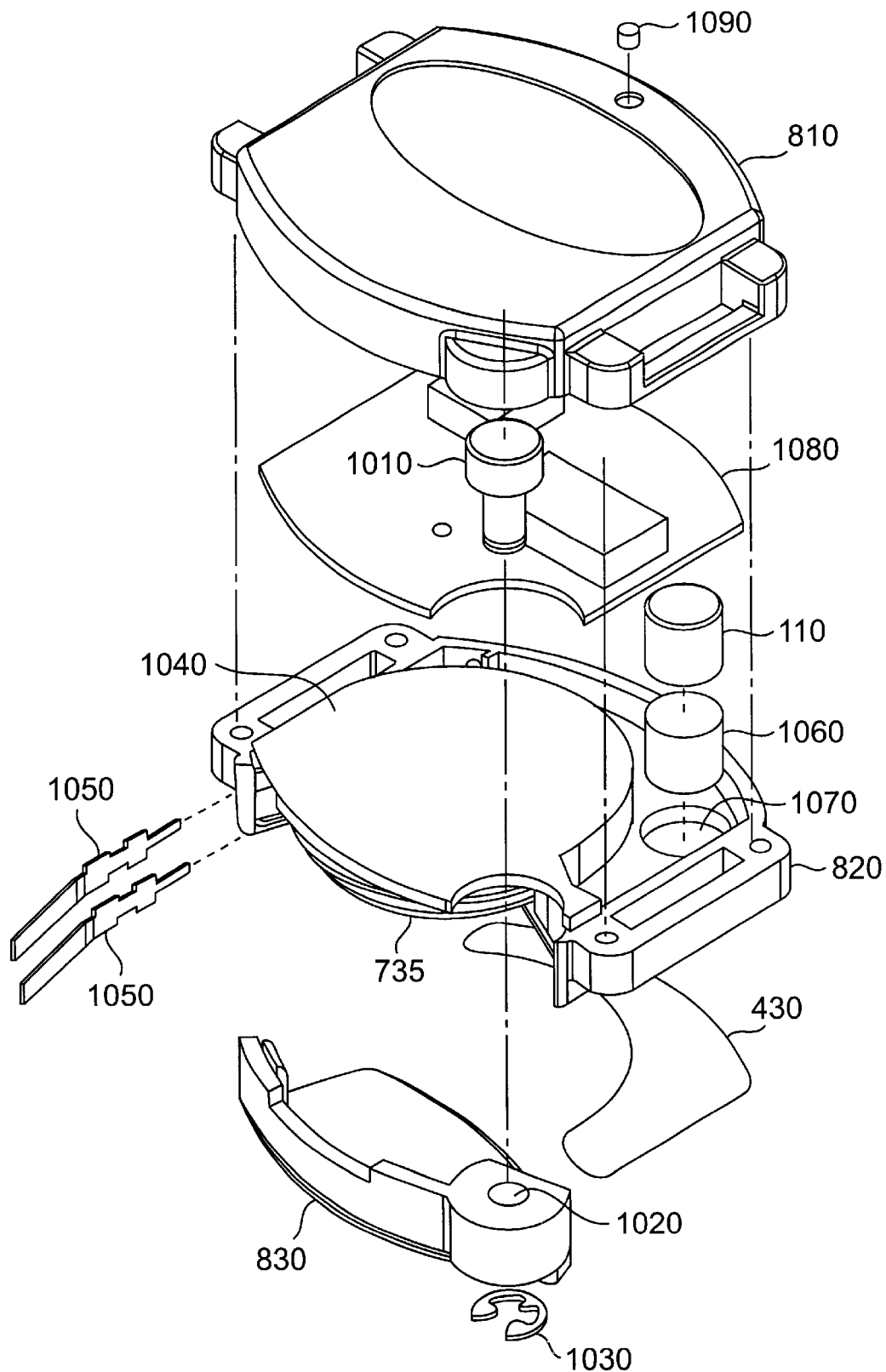
FIG. 10 is an exploded perspective top view of the monitor housing of the physiological condition monitor showing the interconnection of the components of the monitor housing.

FIG. 10 shows an exploded view of monitor housing 800. Top housing 810 has portions that receive a pivotal hinge boss 1010 and allow hinge boss 1010 to rotate. Hinge boss 1010 pivotally couples battery door 830 to top housing 810 and bottom housing 820. Battery door 830 is formed having portions that define a passageway 1020 through battery door 830 for receiving the lower end of hinge boss 1010. After the lower end of hinge boss 1010 has been placed through passageway 1020 of battery door 830, retaining ring 1030 fastens battery door 830 to hinge boss 1010.

In FIG. 10 battery 735 is shown in position within monitor housing 800. Battery support plate 1040 covers the top of battery 735 and only the lower edge of battery 735 is visible in FIG. 10. Two battery retaining pins 1050 are placed along the interior of bottom housing 820 to keep battery 735 in its place within monitor housing 800 and to contact the positive and negative terminals of battery 735.

Microphone 110 of low frequency microphone sensor 100 is shown in FIG. 10. To support microphone 110 within the structure of monitor housing 800 microphone 110 is placed through microphone sleeve 1060. In this advantageous embodiment of the invention microphone 110 extends through an aperture 1070 in the bottom of chamber 120 and extends into cavity 440. The interior of chamber 120 and cavity 440 are not visible in FIG. 10.

Printed circuit board 1080 supports the electronic circuitry of physiological condition monitor 700 that has been previously described. Lens 1090 is provided to permit a signal light such as a light emitting diode (not shown) to send signals concerning the operational status of physiological condition monitor 700.

Figure 11:
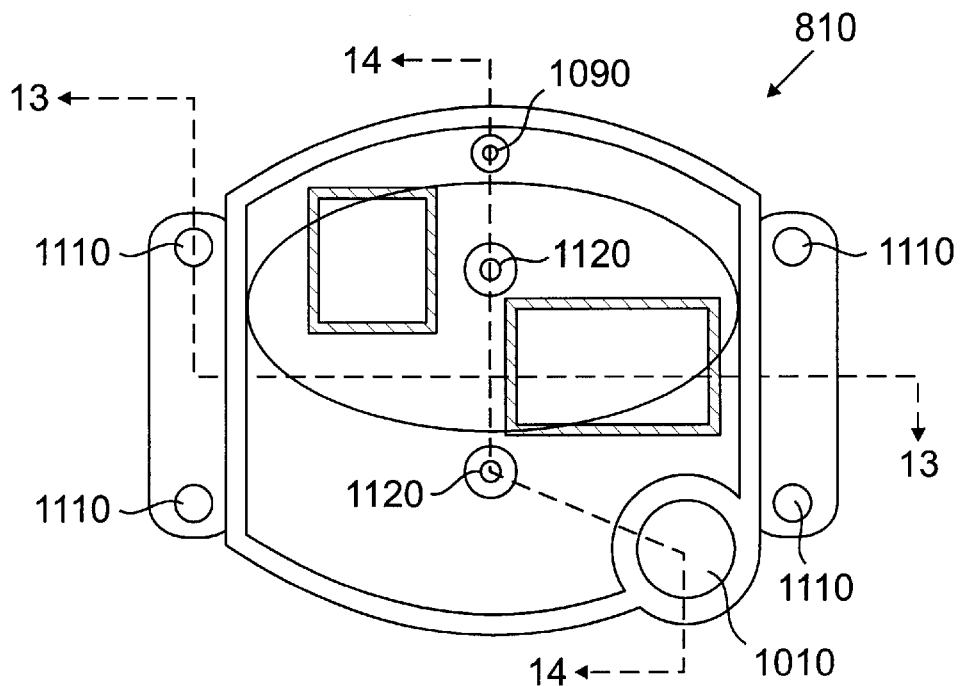
FIG. 11 is a plan view of the top housing of the monitor housing.

FIG. 11 is a plan view of the top housing 810 of monitor housing 800. The location of hinge boss 1010 is shown at one corner of top housing 810. Also shown are the locations of four passageways 1110 for receiving fasteners such as screws (not shown) for fastening top housing 810 to bottom housing 820. The location of lens 1090 is also shown. The rectangles that are shown in dotted outline in the center of the plan view of top housing 810 represent the locations of electronic circuitry (such as processor unit 730) that are mounted on underlying printed circuit board 1080. The two circles that are visible in the center of the plan view of top housing 810 represent the locations of two receptacles 1120 for receiving fasteners such as screws (not shown) for printed circuit board 1080 to top housing 810.

Figure 12:
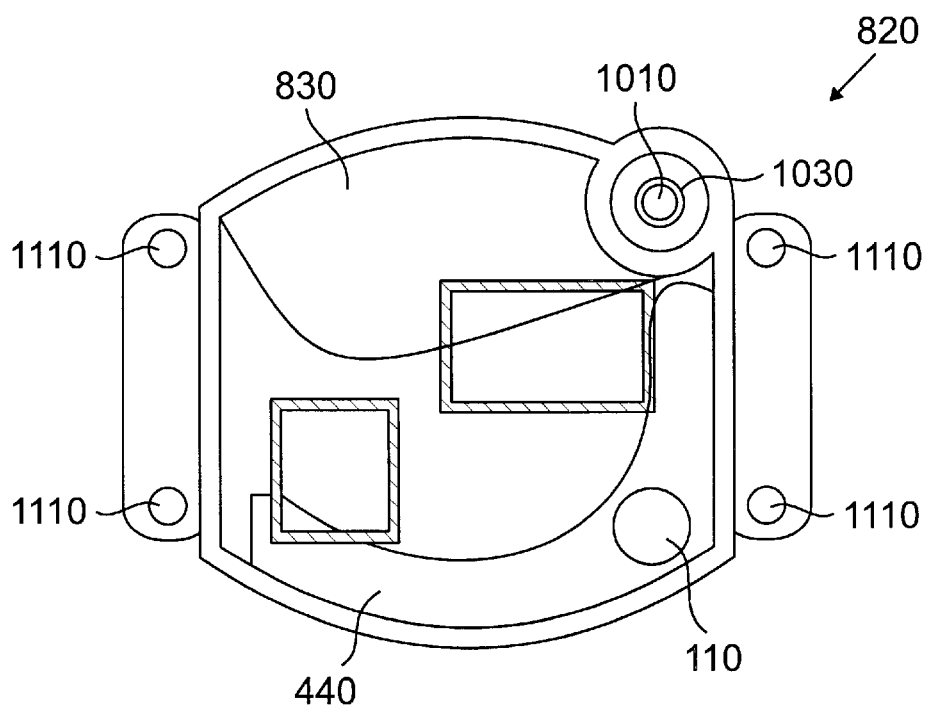
FIG. 12 is a plan view of the bottom of the assembled physiological condition monitor.

FIG. 12 is a plan view of bottom of the assembled monitor housing 800. The location of hinge boss 1010 and retaining ring 1030 is shown at one corner of bottom housing 820. Battery door 830 is shown in its closed position. Also shown are the locations of four passageways 1110 for receiving fasteners such as screws (not shown) for fastening top housing 810 to bottom housing 820. The rectangles that are shown in dotted outline in the center of bottom housing 820 represent the locations of electronic circuitry (such as processor unit 730) that are mounted on underlying printed circuit board 1080. The location of microphone 110 within cavity 440 is also shown. Membrane 430 (not shown in FIG. 12) covers the top of cavity 440.

Figure 13:
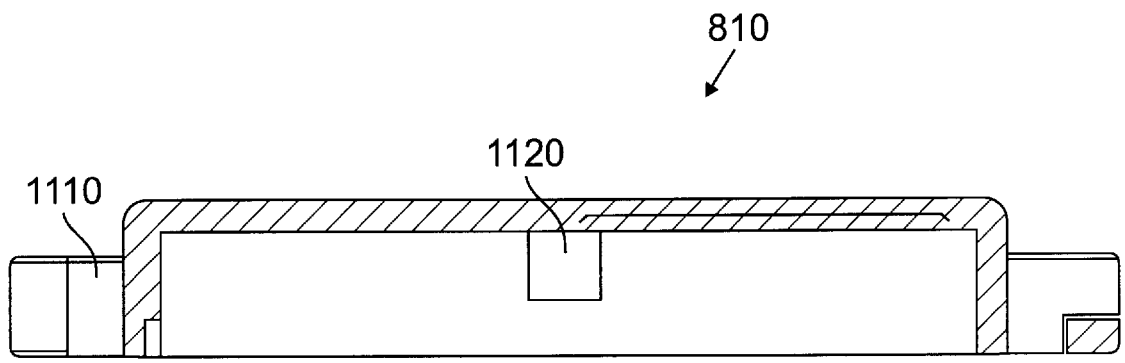
FIG. 13 is a cross sectional view of the top housing of the monitor housing taken along line 13—13 of FIG. 11.
Figure 14:
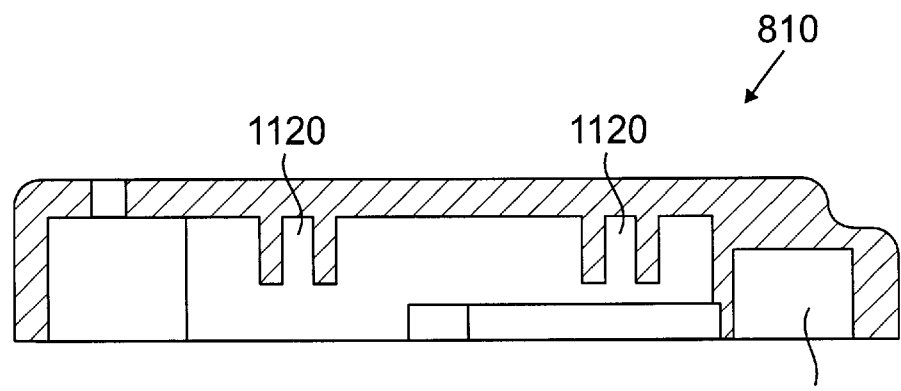
FIG. 14 is a cross sectional view of the top housing of the monitor housing taken along line 14—14 of FIG. 11.

FIG. 13 is a cross sectional view of top housing 810 of monitor housing 800 taken along line 13—13 of FIG. 11. A side view of receptacle 1120 is shown. Because the line 13—13 takes a right angle turn, only one receptacle 1110 is shown. FIG. 14 is a cross sectional view of top housing 810 of monitor housing 800 taken along line 14—14 of FIG. 11. Both receptacles 1320 are shown. Also shown is the location of hinge boss 1010.

Figure 15:
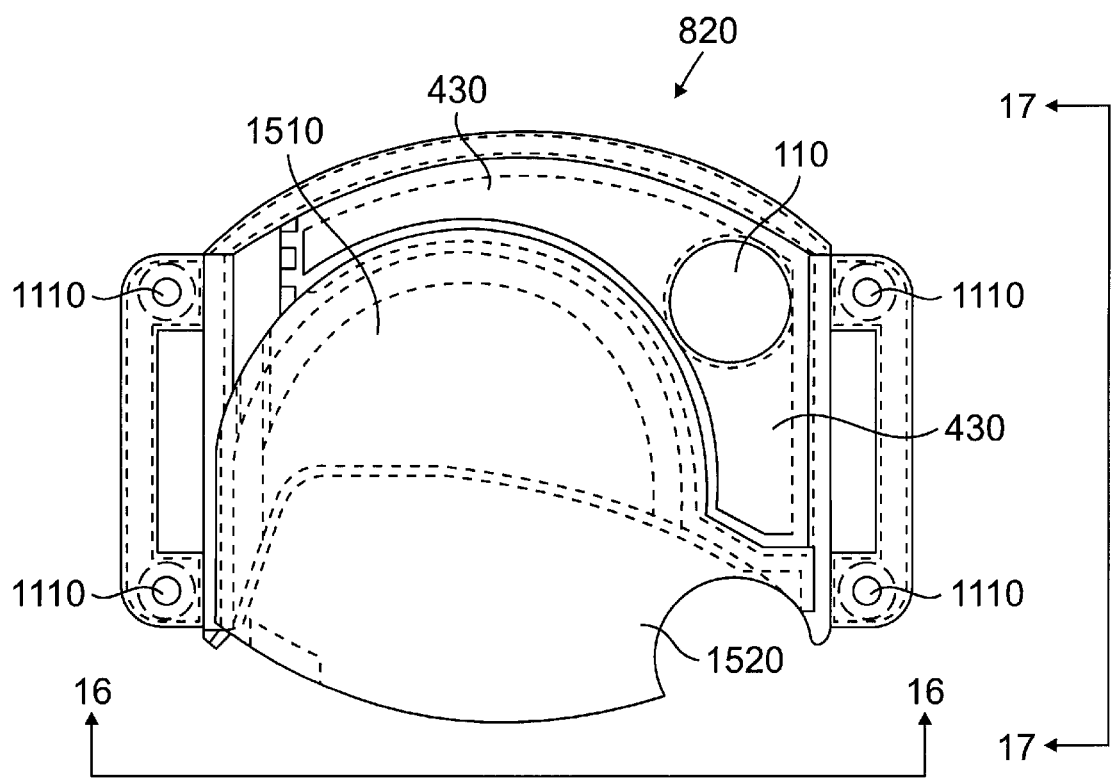
FIG. 15 is a plan view of the bottom housing of the monitor housing.

FIG. 15 is a plan view of bottom housing 820 of monitor housing 800. The location of microphone 110 is shown. Also shown in the location and shape of membrane 430 and the underlying cavity 440 (not shown in FIG. 15). The location of fastener receptacles 1110 are also shown. The circular area 1510 shows the location of battery 735 (not shown in FIG. 15) within monitor housing 800. Oblong area 1520 shows the location of battery door 830 (also not shown in FIG. 15).

Figure 16:
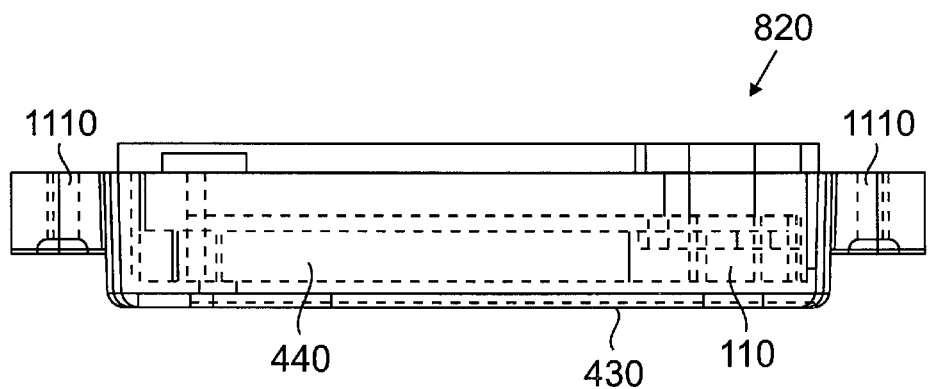
FIG. 16 is a side elevation view of the bottom housing of the monitor housing taken along line 16—16 of FIG. 15.
Figure 17:
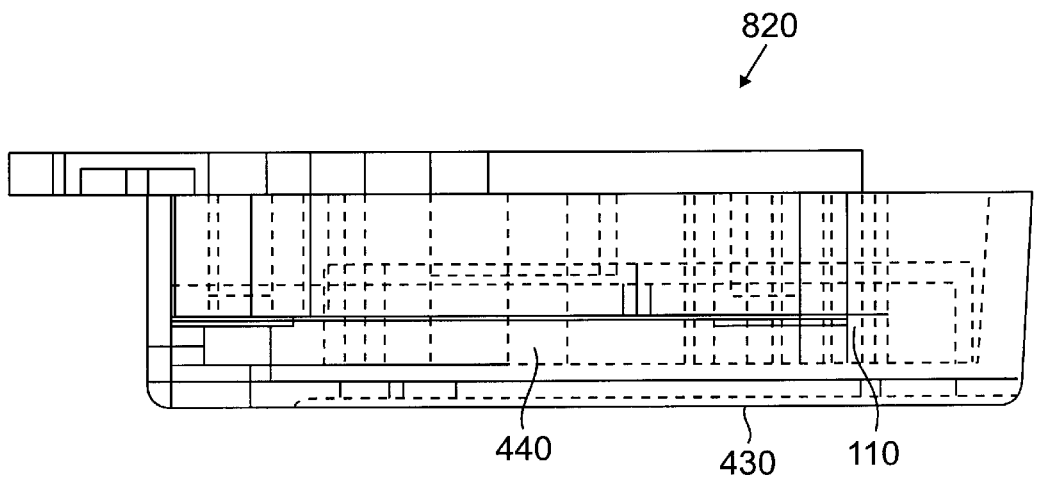
FIG. 17 is an end elevation view of the bottom housing of the monitor housing taken along line 17—17 of FIG. 15.

FIG. 16 is a side elevation view of bottom housing 820 of monitor housing 800 taken along line 16—16 of FIG. 15. A portion of the bottom of bottom housing 820 is covered with membrane 430. The location of cavity 440 in bottom housing 820 is shown. Also shown is the location of microphone 110 and fastener receptacles 1110. FIG. 17 is an end elevation view of bottom housing 820 of monitor housing 800 taken along line 17—17 of FIG. 15. FIG. 17 also shows the location of membrane 430, cavity 440 and microphone 110.

Figure 18:
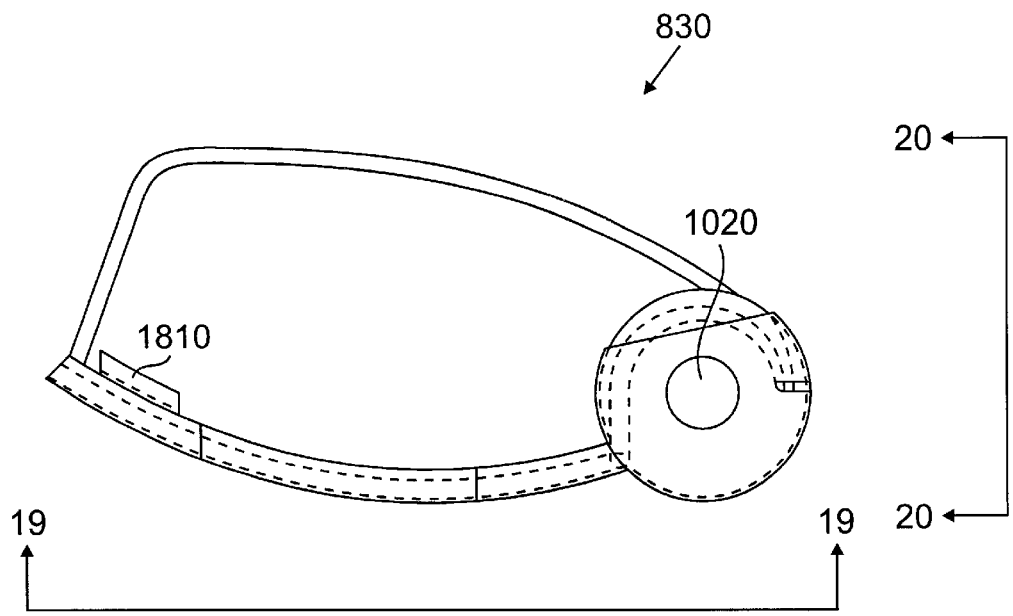
FIG. 18 is a plan view of the battery door of the monitor housing.
Figure 19:
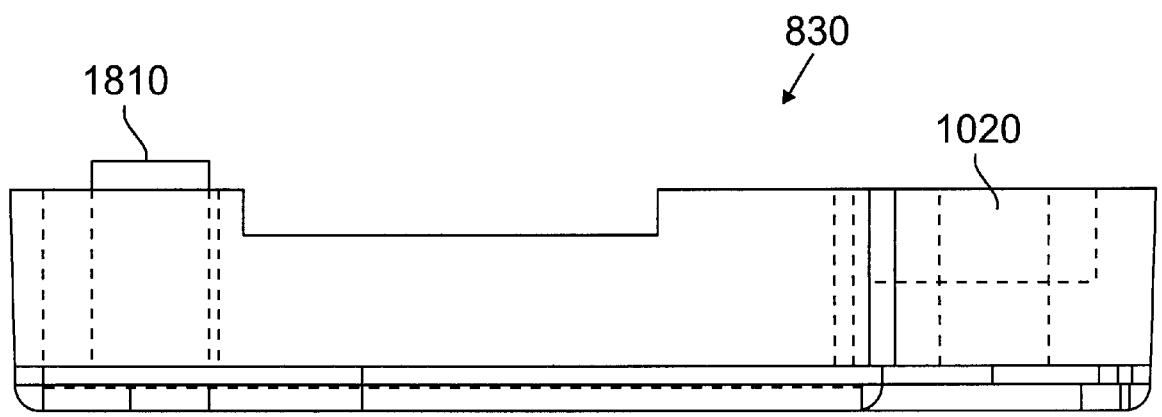
FIG. 19 is a side elevation view of the battery door of the monitor housing taken along line 19—19 of FIG. 18.
Figure 20:
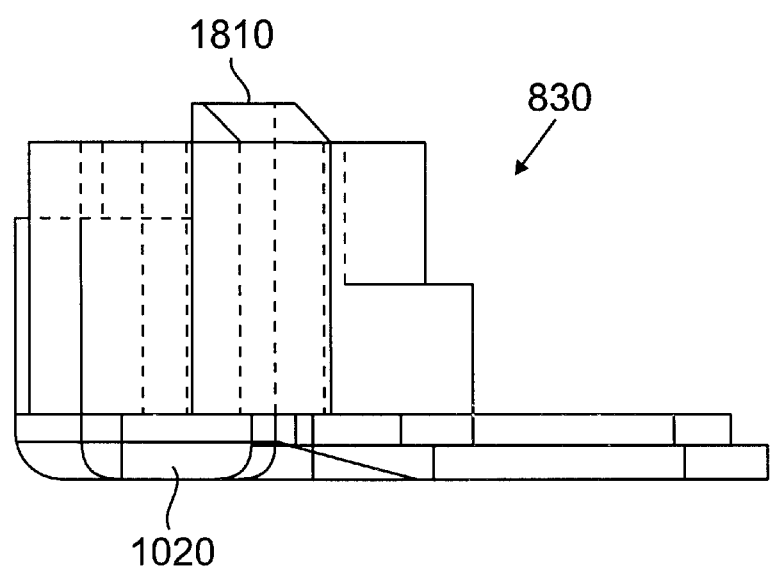
FIG. 20 is an end elevation view of the battery door of the monitor housing taken along line 20—20 of FIG. 18.

FIG. 18 is a plan view of battery door 830 of monitor housing 800. The shape of battery door 830 fits the oblong area 1520 shown in FIG. 15. As previously mentioned, battery door 830 is formed having portions that define a passageway 1020 through battery door 830 for receiving the lower end of hinge boss 1010. Passageway 1020 is shown in FIG. 18. Also shown is latch 1810 for latching battery door 830 after it has been closed. FIG. 19 is a side elevation view of battery door 830 of monitor housing 800 taken along line 19—19 of FIG. 18. FIG. 20 is an end elevation view of battery door 830 of monitor housing 800 taken along line 20—20 of FIG. 18.

Figure 21:
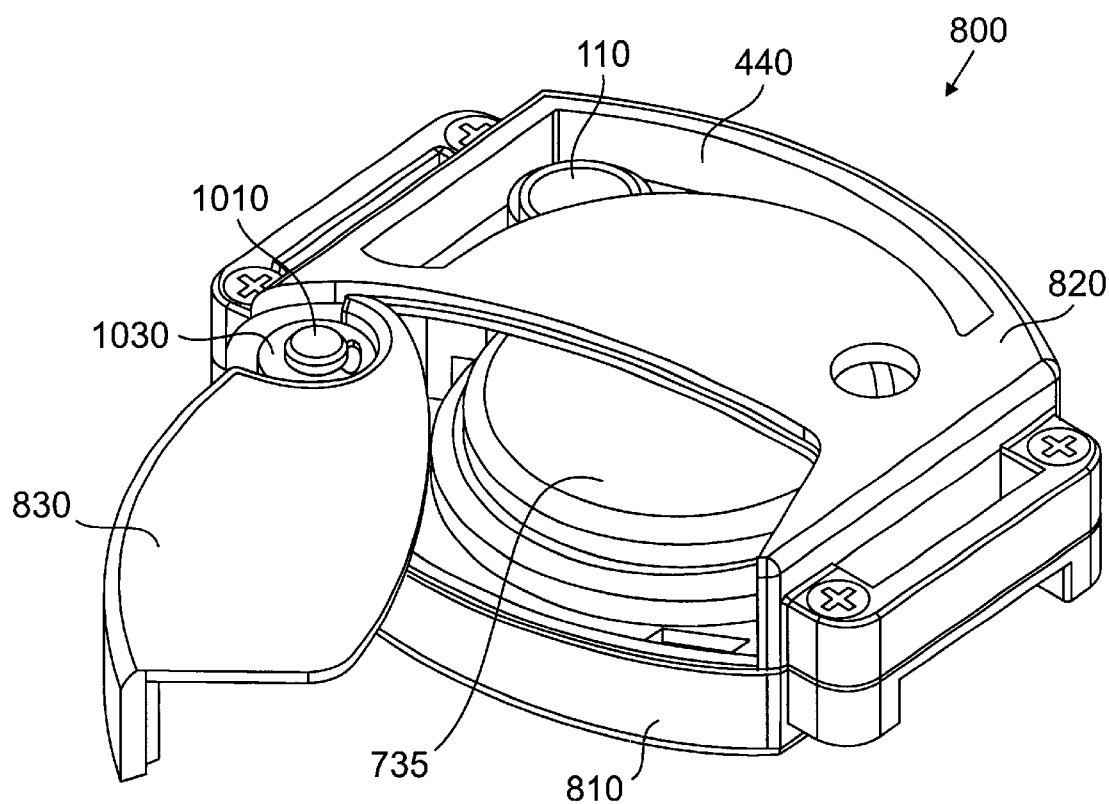
FIG. 21 is a perspective bottom view of the monitor housing showing the battery door in an open position and showing the placement of a battery in the monitor housing.

FIG. 21 is a perspective bottom view of monitor housing 800 of physiological condition monitor 700 showing battery door 830 in an open position and showing the placement of battery 735 in monitor housing 800. The location of microphone 110 within cavity 440 is shown. The end of hinge boss 1010 and retaining ring 1030 are also shown.

The present invention may also be used in conjunction with physiological condition monitors that monitor the movement and position orientation of a body. A physiological condition monitor that monitors the movement and position orientation of a body is described in U.S. patent application Ser. No. 09/396,991 filed Sep. 15, 1999 by Lehrman et al. entitled "Systems for Evaluating Movement of a Body and Methods of Operating the Same." U.S. patent application Ser. No. 09/396,991 is hereby incorporated herein by reference for all purposes.

Figure 22:
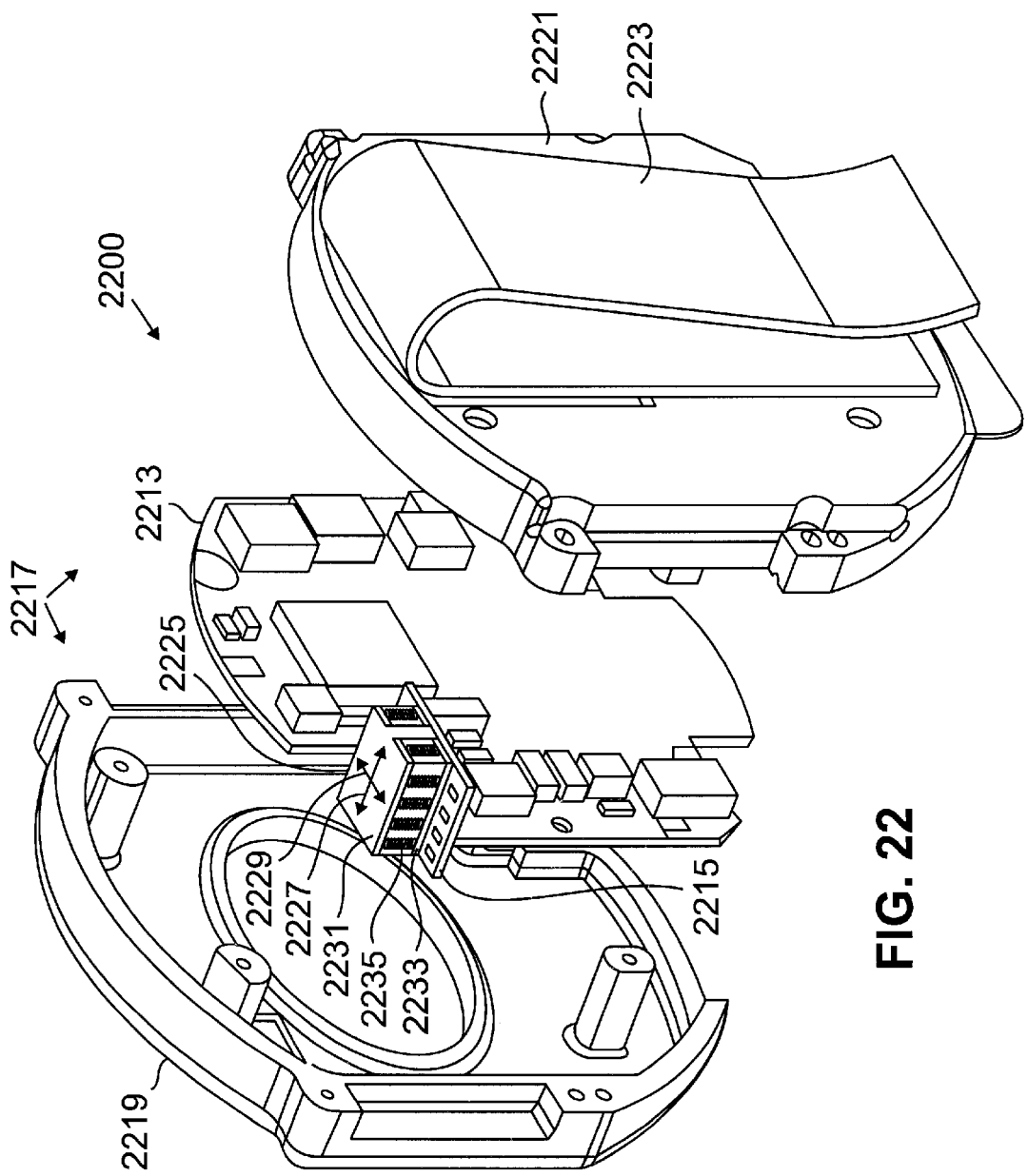
FIG. 22 is an exploded perspective view of a physiological condition monitor for obtaining data relating to the movement and the position orientation of a body.

FIG. 22 is an exploded perspective view of physiological condition monitor 2200 for obtaining data relating to the movement and the position orientation of a body. Monitor 2200 measures and distinguishes selected accelerative events of a body (not shown). As used in this disclosure, the phrases "accelerative events" or "accelerative phenomena" are defined as occurrences of change in velocity of the body (or acceleration), whether in magnitude, direction or both.

Monitor 2200 includes circuit boards 2213 and 2215 (connected boards at right angles to one another) that are associated with a housing (generally designated 2217) utilizing known mounting techniques. Exemplary housing 2217 (and monitor 2200, for that matter), when assembled, is approximately one centimeter thick and is approximately five centimeters across in any direction.

Housing 2217 may comprise, for example, exemplary housing halves 2219 and 2221 that encase boards 2213 and 2215, although those skilled in the art will understand that any configuration suitable for a particular implementation of the invention may be arranged.

Exemplary rear half 2221, is provided with a clip 2223 for associating monitor 2200 with the body (e.g., people, animals, objects of various sorts, etc.). Exemplary clip 2223 is shown as a mechanical spring-type clip, but could be any known attachment device or system, including either mechanical or chemical attachment systems, or any other suitable means for associating monitor 2200 with the body.

Monitor 2200 includes a processor (shown in FIG. 23) and a sensor 2225. Exemplary sensor 2225 operates to sense accelerative phenomena of the body, and is mounted on circuit board 2213 with x and y axes 2227 and 2229, respectively, oriented thereat (though other orientations could be utilized).

Sensor 2225 is illustratively shown as a plural-axis (dual shown) acceleration measuring device suitably mounted on a single monolithic integrated circuit (one conventional sensor is an accelerometer available from Analog Devices, Inc., located at One Technology Way, Norwood, Mass., United States of America, namely, Model No. ADXL202). Sensor 2225 includes polysilicon surface-micromachined sensor layer 2231 built on top of silicon wafer 2233. Polysilicon springs 2235 resiliently suspend sensor layer 2231 over the surface of wafer 2233 providing resistance against acceleration forces. Deflection of the sensor layer is measured using a differential capacitor formed by independent fixed and central plates, the fixed plates driven by 180° out of phase square waves having amplitude proportional to acceleration. Signal outputs from each axis of sensor 2225 are conditioned (i.e., phase sensitive demodulation and low pass filtering) and presented at analog output nodes. While not utilized in the primary advantageous embodiment of this invention, the Analog Devices' accelerometer is operable to convert the analog signals to duty cycle modulated ("DCM") signals at a DCM stage providing digital output signals capable of being directly counted at a processor.

While techniques for reconstructing analog signals from the digital output signals may suitably be utilized (e.g., passing the duty cycle signals though an RC filter), thereby allowing use of the digital signal output of a sensor of monitor 2200 hereof. Use of the analog signal outputs has been found advantageous due to the increased bandwidth availability (0.01 Hz to 5 kHz, adjustable at capacitors at the output nodes to bandlimit the nodes implementing low-pass filtering for antialiasing and noise reduction), and thus measuring sensitivity, attained. A typical noise floor of 500 $\mu$g/Hz is achieved, thereby allowing signals below 5 mg to be resolved for bandwidths below 60 Hz.

According to the illustrated embodiment, sensor 2225 generates analog output voltage signals corresponding to measurements in the x and y axes, which include both an ac voltage component proportional to G forces (i.e., dynamic acceleration component related to vibrations of sensor layer 2231) and a dc voltage component proportional to an angle relative to earth (i.e., static acceleration component related to gravity). This open loop acceleration measurement architecture, capable of measuring both static and dynamic acceleration, can thus be utilized to determine position of a body by measuring both the x and y output voltages simultaneously, as well as measure forces of impact experienced by a body. This information comprises state indicia, and utilizing both signal components from both outputs, the sensed accelerative phenomena of the body may subsequently be processed to distinguish a variety of accelerative phenomena and, ultimately, to selectively act based on the distinctions, as is described in detail hereafter to determine whether the evaluated body movement is normal or abnormal, and, if abnormal, whether the same is within tolerance.

It is noted that the foregoing embodiment has been introduced for illustrative purposes only. In alternate embodiments, any sensor that is capable of sensing accelerative phenomena relative to a body may be used in lieu of, or even in conjunction with, sensor 2225. Further, alternate orientations of sensor 2225 may be used for different applications.

Figure 23:
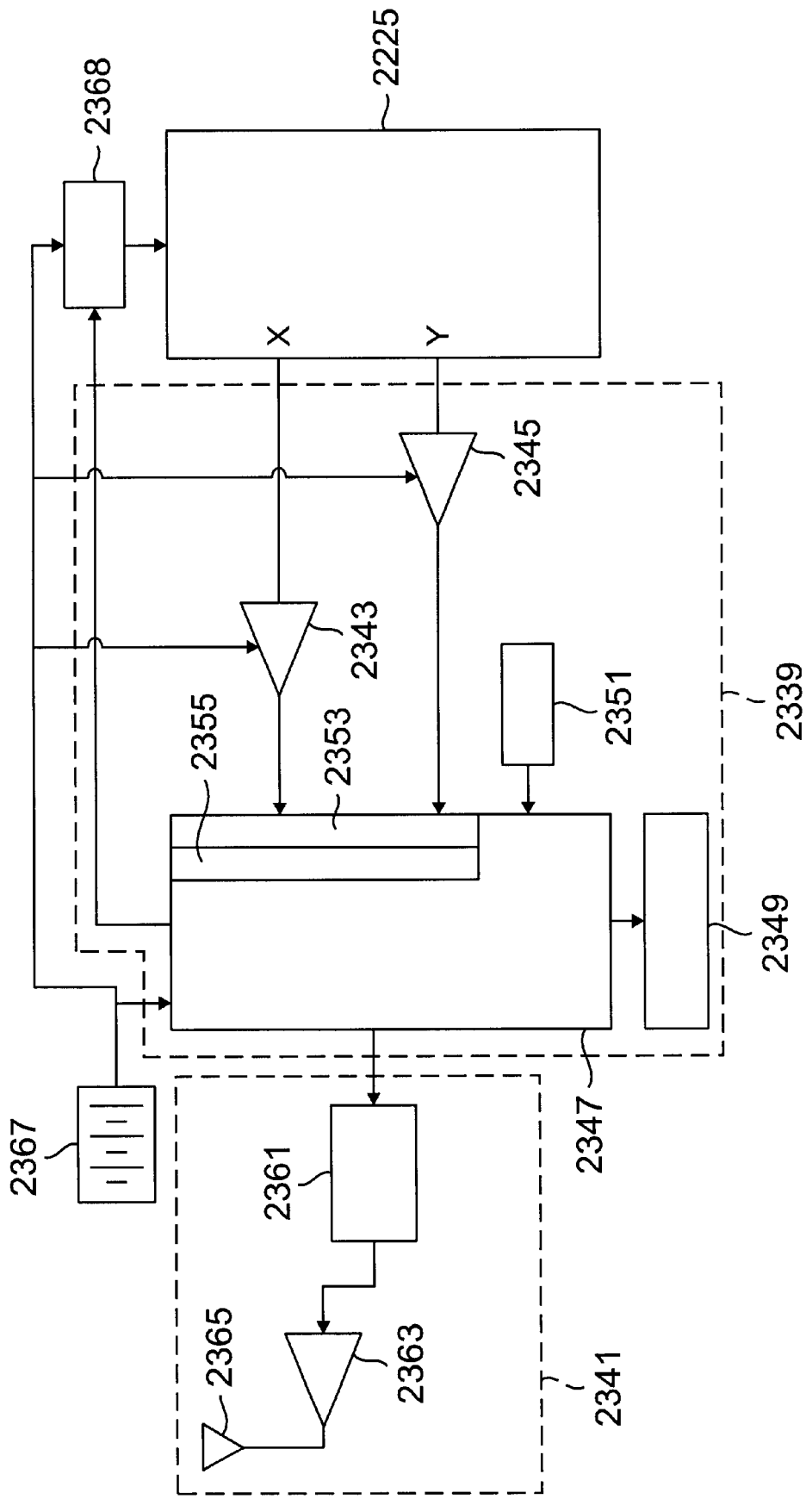
FIG. 23 is a block diagram of one embodiment of the physiological condition monitor shown in FIG. 22 showing the interconnection of the monitor components.

FIG. 23 is a block diagram of one embodiment of physiological condition monitor 2200 showing the interconnection of the monitor components. The illustrated embodiment includes processing circuitry 2339, indicating circuit 2341, power supply 2367, and a switch 2368, along with sensor 2225.

Exemplary processing circuitry 2339 illustratively includes a processor 2347 and buffer amplifiers 2343 and 2345 that buffer the analog x and y outputs from sensor 2225. Exemplary processor 2347, which is associated with sensor 2225, is capable of processing the sensed accelerative phenomena as a function of at least one accelerative event characteristic to thereby determine whether an evaluated body movement is within environmental tolerance. Processor 2347 also preferably generates state indicia while processing the sensed accelerative phenomena, which may represent the state of the body within the environment over time. Processor 2347 is associated with a crystal oscillator/clock 2349, switch (DIP) inputs 2351, an analog-digital conversion circuitry 2353 and a DSP filter 2355 (one conventional processor is available from Texas Instruments, Inc., located in Dallas, Tex., United States of America, namely, Model No. MSP430P325).

Exemplary indicating circuit 2341, in response to direction from processor 2347, is operable to at least one of initiate an alarm event; communicate such state, or tolerance, indicia to a monitoring controller; generate statistics; etc. Indicating circuit 2341 may take any number of forms, however, for use in monitor 2200 of one advantageous embodiment, stage 2341 is an RF transmitter including RF modulator 2361 enabled by processor 2347. Exemplary data is presented and modulated at modulator 2361, amplified at amplifier 2363 and transmitted at antenna 2365 (to a remote receiver unit as discussed hereinafter).

According to the present embodiment, power for the various components of monitor 2200 is provided by power supply 2367, which illustratively is a 3.6 volt battery. Low power management may suitably be under the control of processor 2347 utilizing exemplary switched/power supply voltage FET switch 2368 at sensor 2225, which provides power only during sampling cycles, and operates to shut components down during non-use cycles. For instance, processor 2347 may be taken off-line when processing is complete, reducing current drain.

It should be noted that the various circuitry discussed heretofore has been introduced herein for illustrative purposes only. Monitor 2200 may be implemented using any suitably arranged computer or other processing system including micro, personal, mini, mainframe or super computers, as well as network combinations of two or more of the same. In point of fact, in one advantageous embodiment, sensor 2225 and processor 2347 are not co-located, but rather associated wirelessly. To that end, the principles of the present invention may be implemented in any appropriately arranged device having processing circuitry. Processing circuitry may include one or more conventional processors, programmable logic devices, such as programmable array logic ("PALs") and programmable logic arrays ("PLAs"), digital signal processors ("DSPs"), field programmable gate arrays ("FPGAs"), application specific integrated circuits ("ASICs"), large scale integrated circuits ("LSIs"), very large scale integrated circuits ("VLSIs") or the like, to form the various types of circuitry, processors, controllers or systems described and claimed herein.

A detailed description of the method of operation of monitor 2200 is set forth in previously referenced U.S. patent application Ser. No. 09/396,991 filed Sep. 15, 1999 by Lehrman et al. entitled "Systems for Evaluating Movement of a Body and Methods of Operating the Same."

Figure 24:
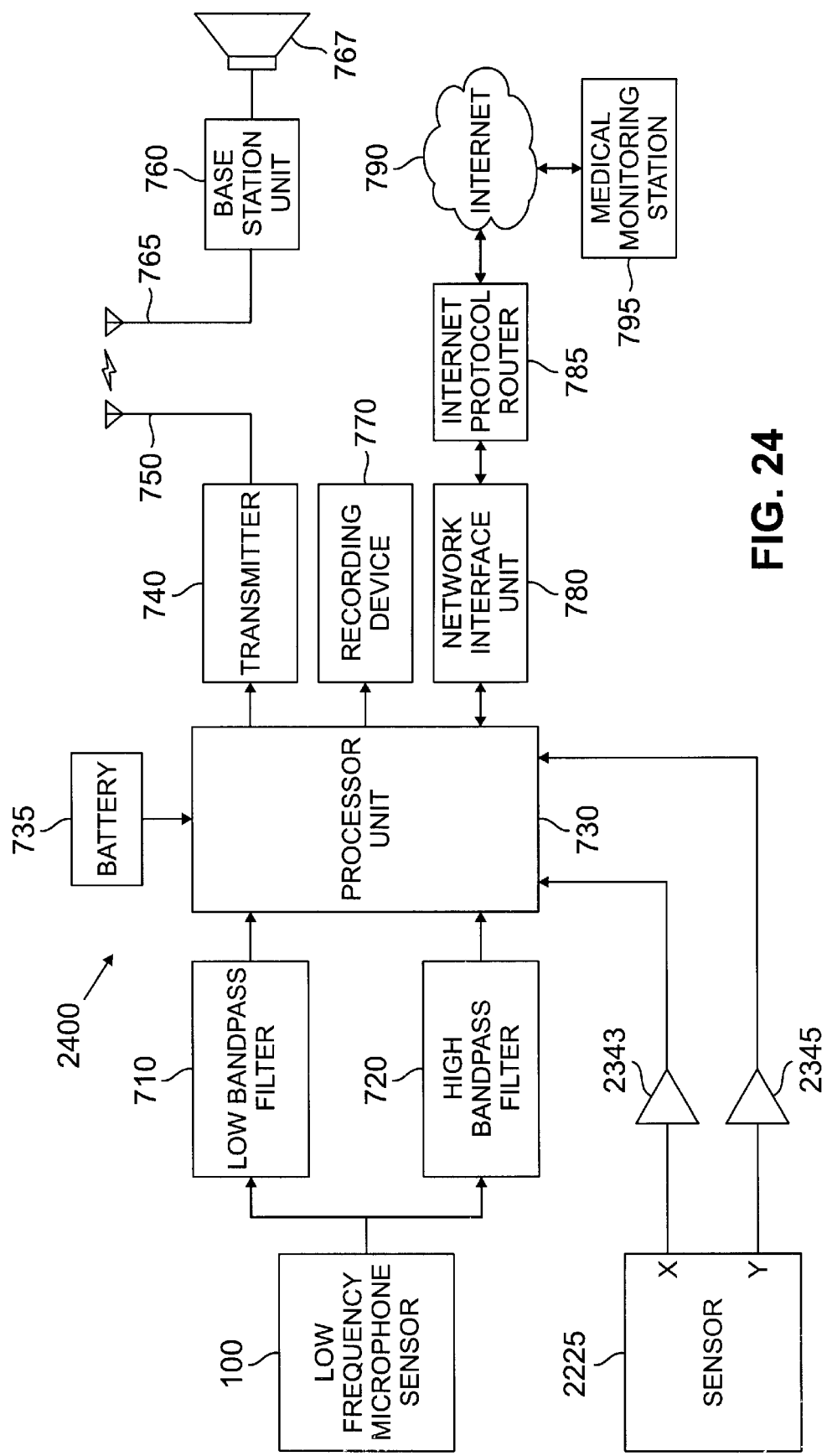
FIG. 24 is a block diagram of one embodiment of a physiological condition monitor for obtaining data relating to the cardiac activity and the respiration activity and the movement and position orientation a person's body.

FIG. 24 is a block diagram of one embodiment of physiological condition monitor 2400 utilized in conjunction with the present invention. In one embodiment of the present invention sensor 2225 is housed in housing 2217 as previously described and coupled to processor unit 730 through wiring (not shown) that connects housing 2217 with monitor housing 800. In another embodiment of the present invention, sensor 2225 and its associated circuitry are mounted directly on printed circuit board 1080 of monitor housing 800.

These embodiments are illustrated in FIG. 24 in block diagram form as physiological condition monitor 2400. This particular exemplary embodiment of physiological condition monitor 2400 shows sensor 2225 coupled to processor 730 via buffer amplifier 2343 and buffer amplifier 2345. Although battery 735 is shown coupled only to processor 730, it is actually is coupled to and supplies electrical power to all of the other components in embodiment 2400 via other electrical connections (not shown).

Movement and position data from sensor 2225 may be stored and utilized by processor unit 730 in accordance with the principles that have previously been described. Specifically, processor 730 is coupled to recording device 770. Processor 730 is capable of sending movement and position data signals from sensor 2225 directly to recording device 770.

Alternatively, the movement and position data from sensor 2225 may be transmitted via transmitter 740 and antenna 750 to base station unit 760. Alternatively, the movement and position data from sensor 2225 may be sent to medical monitoring station 795 via network interface unit 780, Internet protocol router 785 and the Internet 790, as previously described.

As shown in FIG. 24, sensor 2225 may be coupled to processor 730 along with physiological information from other physiological condition monitors such as respiration signals from the low bandpass filter 710 and cardiac signals from high bandpass filter 720. Other types of physiological condition monitors may also be utilized concurrently. In this manner different types of data may be collected simultaneously for the purpose of facilitating subsequent studies to correlate the data.

Although the present invention has been described with reference to monitoring the physiological conditions of human beings, the present invention can also be used to monitor the physiological conditions of vertebrate animals such as dogs, cats, horses, and the like.

Although the present invention has been described in detail, those skilled in the art should understand that they can make various changes, substitutions and alterations herein without departing from the spirit and scope of the invention in its broadest form.

What is claimed is:

1. An apparatus for detecting very low frequency acoustic signals and signals indicative of body orientation comprising:
   a low frequency sensor capable of being acoustically coupled to a source of low frequency acoustic signals, said low frequency sensor capable of receiving low frequency acoustic signals in the frequency range of one tenth Hertz to thirty Hertz and generating electronic signals indicative of the intensity of said low frequency acoustic signals; and
   an apparatus capable of evaluating movement of a body relative to an environment of the type comprising:
   a sensor, associable with said body, that senses accelerative phenomena of said body; and
   a processor, associated with said sensor, that processes said sensed accelerative phenomena as a function of at least one accelerative event characteristic to thereby determine whether said evaluated body movement is within environmental tolerance.

2. An apparatus as claimed in claim 1 further comprising signal processing circuitry coupled to said low frequency sensor capable of processing said electronic signals from said low frequency sensor to obtain electronic signals indicative of the intensity of said low frequency acoustic signals in the frequency range of one tenth Hertz to two Hertz.

3. An apparatus as claimed in claim 1 further comprising signal processing circuitry coupled to said low frequency sensor capable of processing said electronic signals from said low frequency sensor to obtain electronic signals indicative of the intensity of said low frequency acoustic signals in the frequency range of ten Hertz to thirty Hertz.

4. The apparatus as claimed in claim 1 wherein said low frequency sensor comprises:
   a chamber capable of being acoustically coupled to a source of acoustic signals, said chamber having portions that define a cavity within said chamber; and
   a microphone capable of receiving low frequency acoustic signals within said cavity of said chamber in the frequency range of one tenth Hertz to thirty Hertz and capable of generating electronic signals indicative of the intensity of said low frequency acoustic signals.

5. The apparatus as claimed in claim 4 wherein said chamber is a closed chamber filled with fluid.

6. The apparatus as claimed in claim 5 wherein said fluid is air.

7. The apparatus as claimed in claim 4 wherein said chamber is an open chamber filled with air.

8. The apparatus as claimed in claim 4 wherein said chamber is formed having nonrigid walls.

9. The apparatus as claimed in claim 8 wherein said nonrigid walls are capable of moving inwardly and outwardly with respect to the interior of said cavity in response to the presence of low frequency acoustic energy.

10. An apparatus as claimed in claim 4 further comprising signal processing circuitry coupled to said microphone capable of processing said electronic signals from said microphone to obtain electronic signals indicative of the intensity of said low frequency acoustic signals in the frequency range of one tenth Hertz to two Hertz.

11. An apparatus as claimed in claim 4 further comprising signal processing circuitry coupled to said microphone capable of processing said electronic signals from said microphone sensor to obtain electronic signals indicative of the intensity of said low frequency acoustic signals in the frequency range of ten Hertz to thirty Hertz.

12. An apparatus for detecting very low frequency acoustic signals and signals indicative of body orientation comprising:
   an apparatus capable of detecting very low frequency acoustic signals in the frequency range of one tenth Hertz to thirty Hertz comprising:
   a chamber capable of being acoustically coupled to a source of acoustic signals, said chamber having portions that define a cavity within said chamber, and said chamber having nonrigid walls capable of moving inwardly and outwardly with respect to the interior of said cavity in response to the presence of low frequency acoustic energy;

a microphone placed within said cavity of said chamber capable of receiving low frequency acoustic signals within said cavity of said chamber that are caused by the inward and outward motion of said nonrigid walls of said cavity, and capable of generating electronic signals indicative of the intensity of said low frequency acoustic signals; and an apparatus capable of evaluating movement of a body relative to an environment of the type comprising:
  a sensor, associable with said body, that senses accelerative phenomena of said body; and
  a processor, associated with said sensor, that processes said sensed accelerative phenomena as a function of at least one accelerative event characteristic to thereby determine whether said evaluated body movement is within environmental tolerance.

13. The apparatus as claimed in claim 4 further comprising:
  a membrane attached to said chamber covering said cavity of said chamber, said membrane capable of moving in response to very low frequency acoustic signals incident on said membrane to cause said very low frequency acoustic signals to be transmitted through said cavity to said microphone.

14. The apparatus as claimed in claim 13 wherein the movements of said membrane amplify the intensity of said very low frequency acoustic signals within said cavity.

15. The apparatus as claimed in claim 14 wherein said movements of said membrane amplify the intensity of said very low frequency acoustic signals within said cavity by causing said very low frequency acoustic signals to resonate within said cavity.

16. An apparatus as claimed in claim 13 further comprising signal processing circuitry coupled to said microphone capable of processing said electronic signals from said microphone to obtain electronic signals indicative of the intensity of said low frequency acoustic signals in the frequency range of one tenth Hertz to two Hertz.

17. An apparatus as claimed in claim 13 further comprising signal processing circuitry coupled to said microphone capable of processing said electronic signals from said microphone sensor to obtain electronic signals indicative of the intensity of said low frequency acoustic signals in the frequency range of ten Hertz to thirty Hertz.

18. The apparatus as claimed in claim 12 further comprising:
  a membrane attached to said chamber covering said cavity of said chamber, said membrane capable of moving in response to very low frequency acoustic signals incident on said membrane to cause said very low frequency acoustic signals to be transmitted through said cavity to said microphone.

19. The apparatus as claimed in claim 18 wherein the movements of said membrane amplify the intensity of said very low frequency acoustic signals within said cavity.

20. The apparatus as claimed in claim 19 wherein said movements of said membrane amplify the intensity of said very low frequency acoustic signals within said cavity by causing said very low frequency acoustic signals to resonate within said cavity.

21. A physiological condition monitor for detecting very low frequency acoustic signals of a person and signals indicative of a person's body orientation comprising:
  a sensor capable of being acoustically coupled to the body of the person being monitored and capable of receiving low frequency acoustic signals in the range of one tenth Hertz to thirty Hertz and capable of generating electronic signals indicative of the intensity of said low frequency acoustic signals; and a low bandpass filter coupled to said sensor capable of processing said electronic signals from said sensor to obtain digitally encoded electronic signals indicative of the intensity of said low frequency acoustic signals in the frequency range of one tenth Hertz to two Hertz, said digitally encoded electronic signals being indicative of respiration activity of the person being monitored; and an apparatus capable of evaluating movement of a person's body relative to an environment of the type comprising:
    a sensor, associable with said body, that senses accelerative phenomena of said body; and
    a processor, associated with said sensor, that processes said sensed accelerative phenomena as a function of at least one accelerative event characteristic to thereby determine whether said evaluated body movement is within environmental tolerance.

22. The physiological condition monitor claimed in claim 21 further comprising:
  a high bandpass filter coupled to said sensor capable of processing said electronic signals from said sensor to obtain digitally encoded electronic signals indicative of the intensity of said low frequency acoustic signals in the frequency range of ten Hertz to thirty Hertz, said digitally encoded electronic signals being indicative of cardiac activity of the person being monitored.

23. The physiological condition monitor claimed in claim 22 further comprising:
  a processor unit, said processor unit coupled to said low bandpass filter capable of receiving said digitally encoded electronic signals from said low bandpass filter indicative of said respiration activity, and said processor unit coupled to said high bandpass filter capable of receiving said digitally encoded electronic signals from said high bandpass filter indicative of said cardiac activity; and
  a recording device associated with said processor unit capable of receiving from said processor unit digitally encoded electronic signals representative of at least one physiological condition and capable of recording said electronic signals.

24. The physiological condition monitor as claimed in claim 23 further comprising a transmitter coupled to said processor unit capable of receiving digitally encoded electronic signals indicative of at least one physiological condition, said transmitter including an antenna for transmitting said digitally encoded electronic signals received from said processor unit.

25. An apparatus for detecting very low frequency acoustic signals from a person and signals indicative of a person's body orientation without being directly coupled to the skin of the person, said apparatus comprising:
  a chamber having portions that define a cavity within said chamber, said chamber capable of being acoustically coupled to low frequency acoustic signals of the person;
  a microphone placed within said cavity of said chamber, said microphone capable of receiving low frequency acoustic signals in the frequency range of one tenth Hertz to thirty Hertz and generating electronic signals indicative of the intensity of said low frequency acoustic signals received by said microphone; and a membrane attached to said chamber covering said cavity of said chamber, said membrane capable of moving in response to very low frequency acoustic signals incident upon said membrane to cause said very low frequency acoustic signals to be transmitted through said cavity to said microphone, said membrane capable of being acoustically coupled to said low frequency acoustic signals of the person without directly contacting the skin of the person; and an apparatus capable of evaluating movement of a person's body relative to an environment of the type comprising:

a sensor, associable with said body but not directly in contact with the skin of the body of said person, that senses accelerative phenomena of said body; and a processor, associated with said sensor, that processes said sensed accelerative phenomena as a function of at least one accelerative event characteristic to thereby determine whether said evaluated body movement is within environmental tolerance.

26. A method for detecting very low frequency acoustic signals and signals indicative of body orientation comprising the steps of:

acoustically coupling a low frequency sensor to a source of low frequency acoustic signals;

receiving in said low frequency sensor acoustic signals in the range of one tenth Hertz to thirty Hertz;

generating in said low frequency sensor electronic signals indicative of the intensity of said low frequency acoustic signals; and processing repeatedly sensed accelerative phenomena of a body as a function of at least one accelerative event characteristic to thereby determine whether said evaluated body movement is within environmental tolerance.

27. A method as claimed in claim 26 further comprising the step of:

processing said electronic signals from said low frequency sensor with signal processing circuitry; and obtaining electronic signals indicative of the intensity of said low frequency acoustic signals in the frequency range of one tenth Hertz to two Hertz.

28. A method as claimed in claim 26 further comprising the step of:

processing said electronic signals from said low frequency sensor with signal processing circuitry; and obtaining electronic signals indicative of the intensity of said low frequency acoustic signals in the frequency range of ten Hertz to thirty Hertz.

29. A method for detecting low frequency acoustic signals and signals indicative of body orientation comprising the steps of:

forming a chamber having portions that define a cavity within said chamber;

placing a microphone within said cavity of said chamber;

acoustically coupling said chamber to a source of low frequency acoustic signals;

receiving in said microphone acoustic signals in the range of one tenth Hertz to thirty Hertz;

generating in said microphone electronic signals indicative of the intensity of said low frequency acoustic signals; and processing repeatedly sensed accelerative phenomena of a body as a function of at least one accelerative event characteristic to thereby determine whether said evaluated body movement is within environmental tolerance.

30. A method as claimed in claim 29 comprising the further steps of:

forming the walls of said chamber with nonrigid material capable of moving inwardly and outwardly with respect to the interior of said cavity in response to the presence of low frequency acoustic energy; and receiving in said microphone acoustic signals in the range of one tenth Hertz to thirty Hertz within said cavity of said chamber that are caused by the inward and outward motion of said nonrigid walls of said cavity.

31. A method for detecting low frequency acoustic signals and signals indicative of body orientation comprising the steps of:

forming a chamber having portions that define a cavity within said chamber;

placing a microphone within said cavity of said chamber;

attaching a membrane to said chamber wherein said membrane covers said cavity of said chamber and wherein said membrane is capable of moving in response to very low frequency acoustic signals incident on said membrane;

acoustically coupling said membrane to a source of low frequency acoustic signals;

receiving in said microphone acoustic signals in the range of one tenth Hertz to thirty Hertz within said cavity of said chamber that are caused by the movements of said membrane;

generating in said microphone electronic signals indicative of the intensity of said low frequency acoustic signals; and processing repeatedly sensed accelerative phenomena of a body as a function of at least one accelerative event characteristic to thereby determine whether said evaluated body movement is within environmental tolerance.

32. A method as claimed in claim 31 comprising the further steps of:

amplifying said low frequency acoustic signals within said cavity of said chamber; and receiving in said microphone said amplified acoustic signals in the range of one tenth Hertz to thirty Hertz.

33. A method for detecting low frequency acoustic signals and signals indicative of body orientation comprising the steps of:

forming a chamber having portions that define a cavity within said chamber;

placing a microphone within said cavity of said chamber;

attaching a membrane to said chamber covering said cavity of said chamber;

acoustically coupling said membrane to a source of acoustic signals;

receiving in said microphone low frequency acoustic signals in the range of one tenth Hertz to thirty Hertz;

generating in said microphone electronic signals indicative of the intensity of said low frequency acoustic signals; and processing repeatedly sensed accelerative phenomena of a body as a function of at least one accelerative event characteristic to thereby determine whether said evaluated body movement is within environmental tolerance.

34. The method as claimed in claim 33 further comprising the steps of:

coupling a low bandpass filter to said microphone capable of processing said electronic signals from said microphone;

obtaining digitally encoded electronic signals indicative of the intensity of said low frequency acoustic signals in the frequency range of one tenth Hertz to two Hertz;

coupling a high bandpass filter to said microphone capable of processing said electronic signals from said microphone; and obtaining digitally encoded electronic signals indicative of the intensity of said high frequency acoustic signals in the frequency range of ten Hertz to thirty Hertz.

35. The method as claimed in claim 34 further comprising the steps of:

coupling a processor unit to said low bandpass filter and to said high bandpass filter;

receiving in said processor unit said digitally encoded electronic signals from said low bandpass filter;

receiving in said processor unit said digitally encoded electronic signals from said high bandpass filter;

coupling a recording device to said processor unit; and receiving in said recording device said digitally encoded electronic signals from said processor unit; and recording in said recording device said digitally encoded electronic signals.

36. The method as claimed in claim 33 further comprising the steps of:

acoustically coupling said membrane to low frequency acoustic signals of a person; and positioning said membrane so that said membrane does not contact the skin of the person.

* * * * *